United States Patent
Shaffer et al.

(10) Patent No.: US 9,943,840 B2
(45) Date of Patent: Apr. 17, 2018

(54) PROCESS FOR PRODUCING NANOPARTICLES

(71) Applicant: IMPERIAL INNOVATIONS LIMITED, London (GB)

(72) Inventors: Milo Shaffer, Londen (GB); Charlotte Williams, London (GB); Katherine Orchard, London (GB); Neil John Brown, London (GB); Jonathan Weiner, London (GB)

(73) Assignee: IMPERIAL INNOVATIONS LIMITED, London (GB)

( * ) Notice: Subject to any disclaimer, the term of this patent is extended or adjusted under 35 U.S.C. 154(b) by 0 days.

(21) Appl. No.: 14/398,604

(22) PCT Filed: May 3, 2013

(86) PCT No.: PCT/GB2013/051175
§ 371 (c)(1),
(2) Date: Nov. 3, 2014

(87) PCT Pub. No.: WO2013/164650
PCT Pub. Date: Nov. 7, 2013

(65) Prior Publication Data
US 2015/0126359 A1    May 7, 2015

(30) Foreign Application Priority Data
May 4, 2012 (GB) .................................. 1207997.6

(51) Int. Cl.
*B01J 37/00* (2006.01)
*C09C 3/08* (2006.01)
(Continued)

(52) U.S. Cl.
CPC .......... *B01J 37/0072* (2013.01); *B01J 23/06* (2013.01); *B01J 23/72* (2013.01); *B01J 31/0261* (2013.01);
(Continued)

(58) Field of Classification Search
None
See application file for complete search history.

(56) References Cited

U.S. PATENT DOCUMENTS

2005/0202964 A1    9/2005    Cavalcanti et al.
2006/0245998 A1    11/2006    Kahn et al.

FOREIGN PATENT DOCUMENTS

DE    10 2009 029640 A1    4/2011
EP    1 892 218 A1    2/2008
(Continued)

OTHER PUBLICATIONS

Berkesi et al. 'FT-IR studies on the formation of tetrazinc long straight-chain (even-numbered C6•C18) μ4-oxo-hexa-μ-carboxylates from the corresponding bis(carboxylato)zinc compounds'. Inorganica Chimica Acta. 1992, vol. 195, pp. 169-173.
(Continued)

*Primary Examiner* — Yun Qian
(74) *Attorney, Agent, or Firm* — Lathrop Gage LLP; Brian C. Trinque

(57) ABSTRACT

This invention relates to a process for the preparation of surface-functionalised metal oxide, metal sulphide, metal selenide or metal telluride nanoparticles, a process for the preparation of a composite material comprising such nanoparticles, nanoparticles and a composite material produced thereby, the use of such nanoparticles in catalysis and a catalyst comprising such nanoparticles.

5 Claims, 6 Drawing Sheets

(51) Int. Cl.
| | |
|---|---|
| C09C 1/62 | (2006.01) |
| C09C 1/04 | (2006.01) |
| B01J 23/06 | (2006.01) |
| B01J 23/72 | (2006.01) |
| B01J 35/00 | (2006.01) |
| B82Y 30/00 | (2011.01) |
| B01J 31/02 | (2006.01) |
| B01J 31/04 | (2006.01) |
| B01J 31/06 | (2006.01) |
| C07C 29/153 | (2006.01) |
| C07C 29/154 | (2006.01) |
| C01G 1/02 | (2006.01) |
| C01G 9/02 | (2006.01) |
| B82Y 40/00 | (2011.01) |
| B01J 31/22 | (2006.01) |

(52) U.S. Cl.
CPC ............ *B01J 31/04* (2013.01); *B01J 31/06* (2013.01); *B01J 35/0013* (2013.01); *B01J 37/0009* (2013.01); *B82Y 30/00* (2013.01); *C07C 29/153* (2013.01); *C07C 29/154* (2013.01); *C09C 1/043* (2013.01); *C09C 1/627* (2013.01); *C09C 3/08* (2013.01); *B01J 31/2239* (2013.01); *B01J 2231/62* (2013.01); *B01J 2231/625* (2013.01); *B01J 2531/26* (2013.01); *B01J 2540/12* (2013.01); *B01J 2540/527* (2013.01); *B82Y 40/00* (2013.01); *C01G 1/02* (2013.01); *C01G 9/02* (2013.01); *C01P 2002/72* (2013.01); *C01P 2002/82* (2013.01); *C01P 2002/84* (2013.01); *C01P 2004/04* (2013.01); *C01P 2004/51* (2013.01); *C01P 2004/64* (2013.01)

(56) References Cited

FOREIGN PATENT DOCUMENTS

| EP | 1 956 102 A2 | 8/2008 |
|---|---|---|
| WO | 2002/049684 A2 | 6/2002 |
| WO | 2009/067088 A2 | 5/2009 |
| WO | 2010/026668 A1 | 3/2010 |
| WO | 2011/032814 A1 | 3/2011 |

OTHER PUBLICATIONS

Ekwunife et al. 'Properties of molten carboxylates. Part 1.—Electrical conductance and molar volumes of some molten lead and zinc carboxylates'. Journal of the Chemical Society: Faraday Transactions. 1975, vol. 71, pp. 1432-1446.

Gonzalez-Campo et al. 'One-pot, in situ synthesis of ZnO-carbon nanotube-epoxy resin hybrid nanocomposites '. Chem. Comm. 2009, vol. 27, pp. 4034-4036.

Husbands et al. 'A study of the adsorption of stearic acid onto ferric oxide'. Powder Technol. 1971, vol. 5, pp. 31-38.

Li et al. 'Bulk Synthesis of Transparent and Homogeneous Polymeric Hybrid Materials with ZnO Quantum Dots and PMMA'. Adv. Mater. 2007, vol. 19, pp. 4347-4352.

Melian-Cabrera et al. 'Pd-Modified Cu—Zn Catalysts for Methanol Synthesis from CO2/H2 Mixtures: Catalytic Structures and Performance'. Journal of Catalysis. 2002, vol. 210, pp. 285-294.

Meulenkamp 'Synthesis and Growth of ZnO Particles'. J. Phys. Chem. B. 1998, vol. 102, pp. 5566-5572.

Orchard et al. 'Organometallic Route to Surface-Modified ZnO Nanoparticles Suitable for In Situ Nanocomposite Synthesis: Bound Carboxylate Stoichiometry Controls Particle Size or Surface Coverage'. Chemistry of Materials. Jun. 20, 2012, vol. 24, pp. 2443-2448.

Shaitan et al. 'Molecular Dynamics of a Stearic Acid Monolayer,' Biophysics. 1994, vol. 44, pp. 429-434.

Spanhel 'Colloidal ZnO nanostructures and functional coatings: A survey'. J. Sol-Gel. Techn. 2006, vol. 29, pp. 7-24.

International Search Report with Written Opinion corresponding to International Search Report No. PCT/GB2013/051175, dated Aug. 28, 2014.

Blank et al. (2001) "Catalysis of the Epoxy-Carbonyl Reaction," Paper Presented In; The International Waterborne, High-Solids and Powder Coatings Symposium, Feb. 21-23, 2001. New Orleans, LA, 18 pgs.

Wicks et al. (2007) "Epoxy and Phenolic Resins," Ch. 13 In; Organic Coatings: Science and Technology. 3rd Ed. John Wiley and Sons, Inc. pp. 271-294.

Inoue et al. (1974) "High reactivity of the ethyl-zinc group "ethylzinc carboxylate" towards acitive hydrogen compounds," J. Organomet. Chem. 81:17-21.

Orchard et al. (2009) "Pentanuclear Complexes for a Series of Alkylzinc Carboxylates," Organomet. 28:5828-5832.

Polarz et al. (2010) "The molecular path to inorganic materials—Zinc oxide and beyond," Inorg. Chim. Acta. 363:4148-4157.

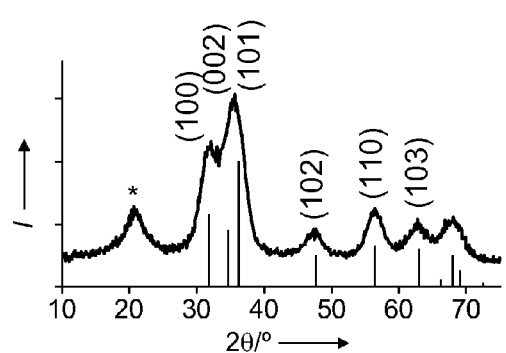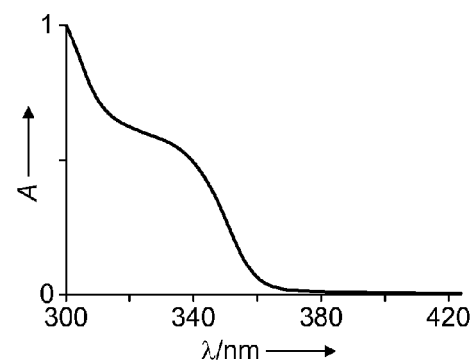
FIG. 3a    FIG. 3b
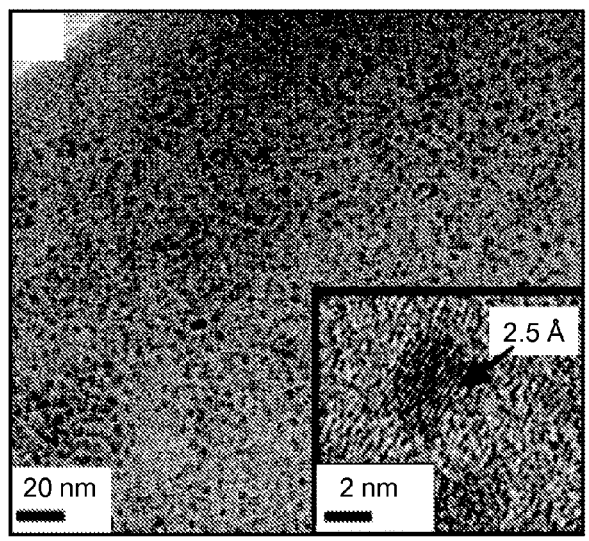
FIG. 3c
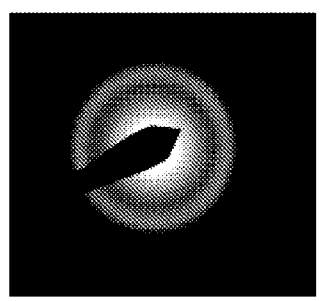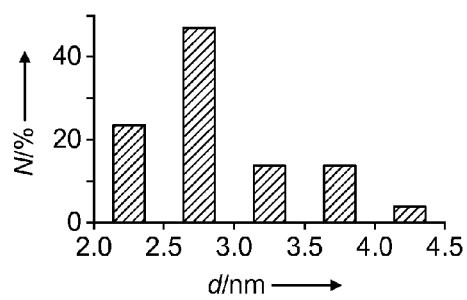
FIG. 3d    FIG. 3e

US 9,943,840 B2

PROCESS FOR PRODUCING NANOPARTICLES

RELATED APPLICATIONS

This application is a 35 U.S.C. § 371 filing of International Application No. PCT/GB2013/051175, filed May 3, 2013, which claims priority to Great Britain Patent Application No. 1207997.6, filed May 4, 2012, each of which is incorporated herein by reference in its entirety.

FIELD

This invention relates to a process for the preparation of surface-functionalised metal oxide, metal sulphide, metal selenide or metal telluride nanoparticles, a process for the preparation of a composite material comprising such nanoparticles, nanoparticles and a composite material produced thereby, the use of such nanoparticles in catalysis and a catalyst comprising such nanoparticles.

BACKGROUND

Metal oxide and other metal chalcogenide nanoparticles are important functional materials having applications, for example, in optoelectronics and catalysis. The properties of such nanoparticles are influenced by particle size, particle shape, defect concentration and surface groups.

ZnO, in the bulk, is a wide bandgap semiconductor, applied in lasing, field effect transistors, gas sensors and in photovoltaics. The optoelectronic properties of ZnO nanoparticles depend on the particle size, defect concentration and surface species; thus control of these factors is important. Zinc oxide, and other metal oxides (and chalcogenides), are also important in catalysis, for example in the synthesis of methanol from syn-gas. Once again, surface chemistry impacts performance.

Control of surface chemistry is also highly relevant in the preparation of nanoparticle-polymer nanocomposites. These materials are applied in electronics, for example as dielectrics, diodes and the active layer in photovoltaics. They are also applied to protect polymers from radiative decay, as, for example, ZnO absorbs UV radiation, and as luminescent materials. In order to optimise the nanocomposite bulk property enhancements, the dispersion of the nanoparticles in a polymer matrix should be maximised, thereby increasing the particle-polymer interfacial area. The development of suitable fabrication methods that minimise particle aggregation is a key goal. Means to prepare the nanoparticles directly within a polymer/pre-polymer mixture (in situ syntheses), are attractive as they can minimise hard agglomerates often formed during handling of particles synthesised ex situ.

In situ nanocomposite syntheses require preparations for nanoparticles that are compatible with the polymer chemistry, i.e. which operate under mild conditions, are tolerant of chemical functionality, and which generate only by products which are compatible with the polymer system or are easy to eliminate. One common route to ZnO nanoparticles is via the alkaline hydrolysis of zinc halides, (L. Spanhel, *J. Sol-Gel Sci. Techn.* 2006, 39, 7-24), often accomplished in alcoholic solvents under ambient conditions. Such 'sol-gel' syntheses have been used to prepare nanocomposites in situ using certain thermoplastic matrices. However, the method is not generally applicable due to the presence of salt by-products and the lack of compatibility with base-sensitive polymer functionalities, common in reactive thermosets. Zinc oxide nanoparticles may also be prepared by the hydrolysis of organozinc precursors and organometallic hydrolyses are chemically tolerant toward a variety of polymer matrices. The "one-pot", in situ preparation of bulk ZnO-epoxy resin nanocomposites with improved thermal conductivity, via the hydrolysis of diethylzinc has recently been reported (A. Gonzalez-Campo, et al, *Chem. Comm.*, 2009, 27, 4034-4036).

Effective modification of the nanoparticle surfaces, either in nanocomposites or as materials in their own right, still remains highly challenging (S. Li, et al, *Adv. Mater.*, 2007, 19, 4347-4352). The most common method to control ZnO surface chemistry is via the application of surfactant ligands which are usually applied in great excess. Excess ligands or reactive small molecules are particularly undesirable in nanocomposites where weak interfaces and plasticisation by free surfactant significantly reduce performance.

It has now been determined that a modified hydrolysis process can be used to produce surface-modified nanoparticles without the need for excess surfactant, structure directing agent or ligand, allowing the achievement of homogenous particle size distribution and with control over surface modification. This process is useful for simple, surface-functionalised nanoparticle production, and is particularly applicable for in situ nanocomposite syntheses in which bulk properties can be enhanced by improving nanoparticle dispersion within the composite. The surface-functionalised nanoparticles also have applications in catalysis, for example in the catalysis of methanol production.

SUMMARY OF THE INVENTION

According to a first aspect of this invention, there is provided a process for the preparation of surface-functionalised metal oxide or metal chalcogenide nanoparticles, the process comprising:
(a) providing a precursor mixture comprising a first organometallic precursor comprising a metal centre M and one or more hydrolysable organic ligands $R^a$, and a source of a non-hydrolysable ligand X, optionally comprising metal centre M, wherein the molar loading, [X]/[M], within the precursor mixture is from 0.001 to 0.4; and
(b) exposing the precursor mixture to $H_2E$, wherein E is O, S, Se or Te, to produce surface-functionalised metal oxide or metal chalcogenide nanoparticles.

In a second aspect, the invention provides a process for the preparation of a composite material comprising surface-functionalised metal oxide or metal chalcogenide nanoparticles dispersed within a polymeric material, the process comprising:
(a) providing a precursor mixture as defined in respect of the first aspect of the invention and combining the precursor mixture with a prepolymer, a thermoplastic or a curable or cured resin;
(b) exposing the mixture produced in step (a) to $H_2E$ wherein E is O, S, Se or Te.

In a third aspect, the invention provides surface-functionalised metal oxide or metal chalcogenide nanoparticles, as produced by a process according to the first aspect of the invention.

In a fourth aspect, the invention provides a composite material comprising surface-functionalised metal oxide or metal chalcogenide nanoparticles dispersed within a polymeric material, as produced by the process of the second aspect of the invention.

In a fifth aspect, the invention provides a surface-functionalised metal oxide or metal chalcogenide nanoparticle (or a population thereof), wherein surface functionalisation comprises ligand X as defined herein bound to the nanoparticle.

In a sixth aspect, the invention provides a process for producing methanol from a gas selected from synthesis gas and a carbon dioxide/hydrogen mixture, comprising exposing the gas to nanoparticles of the third or fifth aspect of the invention.

In a seventh aspect, the invention provides a catalyst comprising nanoparticles of the third or fifth aspect of the invention.

In an eighth aspect, the invention provides a catalyst system comprising nanoparticles of the third or fifth aspect of the invention and a co-catalyst.

In a ninth aspect, the invention provides a process for producing a catalyst, the process comprising providing surface-functionalised metal oxide or metal chalcogenide nanoparticles of the third of fifth aspects of the invention and mixing said nanoparticles with metal nanoparticles in a solvent, preferably an organic solvent.

In a tenth aspect, the invention provides a catalyst as produced by the process of the ninth aspect of the invention.

In an eleventh aspect, the invention provides a composite material comprising a plurality of nanoparticles of the third or fifth aspect of the invention and a polymeric material.

BRIEF DESCRIPTION OF THE DRAWINGS

Specific embodiments of the invention are described below by way of example only and with reference to the accompanying drawings, in which:

FIG. 3 shows data for nanoparticles produced from a 9:1 diethylzinc:zinc bis(stearate) ($ZnSA_2$), in toluene mixture: a) X-ray diffraction pattern, confirming ZnO formation (reference lines from PDF 036-1451, ICDD PDF4+ database); extra peak due to organic component marked with "*"; b) UV-vis spectrum, toluene solution; c) representative TEM image with (inset) individual particle showing (101) lattice planes; d) representative electron diffraction pattern; e) size distribution histogram, measured from multiple TEM images.

DETAILED DESCRIPTION

Figure 1:
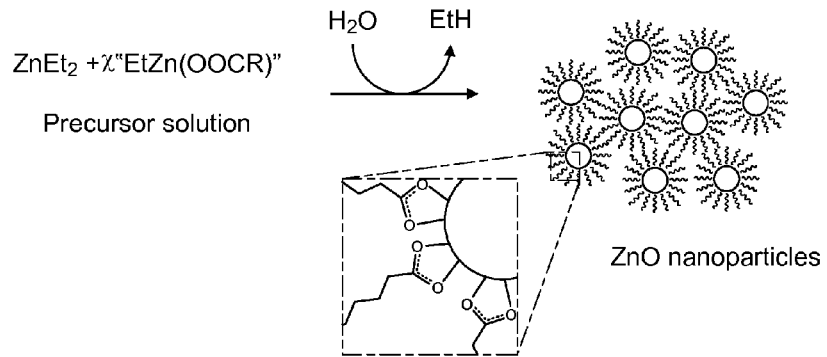
FIG. 1 shows a representation of the reaction occurring to produce ZnO nanoparticles with carboxylate surface functionalisation.

Within this text, the following terminology is used:

The words "comprising" and "comprises" are taken to mean "includes among other things".

A nanoparticle is a particle having at least one dimension of less than 100 nm.

A surface-functionalised metal oxide (or metal chalcogenide, as appropriate) nanoparticle is a metal oxide (or metal chalcogenide) nanoparticle having functional groups bound to the surface thereof (i.e. surface functionalisation). In the context of the present application, surface functionalisation is provided by the non-hydrolysable ligand X. Binding of ligand X to the metal oxide (or metal chalcogenide) nanoparticle surface is covalent. This contrasts to surfactant ligands which non-covalently associate with nanoparticle surface, for example through surface hydroxides on ZnO.

Ligand X may be selected from the group consisting of, but not limited to, a ligand comprising a moiety selected from the group consisting of a carboxylate ($OOCR^1$), a thiocarboxylate ($OSCR^1$ or $SOCR^1$), a dithiocarboxylate ($SSCR^1$), sulphate ($OS(O)_2OR^2$), a sulfonate ($OO_2SR'$), a phosphonate ($O(O)P(OR^2)(R^1)$), a phosphinate ($O(O)PR^2_2$), a halide, a carbonate, a dithiocarbonate, an amine ($—NR^2_2$) and a nitrate. These moieties may provide the point of coordination (i.e. covalent binding) to the metal oxide or metal chalcogenide nanoparticle. It will be appreciated that ligand X may be monodentate, bidentate or polydentate, so may comprise one or more of the moieties listed above, for example as a substituent on the $R^1$ or $R^2$ moiety. $R^1$ may be an optionally substituted aliphatic, heteroaliphatic, aryl or heteroaryl and $R^2$ may be H or a substituent as listed above for $R^1$. In some embodiments, where $R^1$ or $R^2$ is optionally substituted, optional substituents may be selected from the group comprising halide, aliphatic, heteroaliphatic, aryl, heteroaryl, cyanate, epoxide, amine ($—NH_2$, $—NHR^3$, $—NR^3_2$), $—OR^3$ (e.g. $—OMe$), nitro, $—C(O)R^3$ or $—OSiR^3_3$ wherein $R^3$ is optionally substituted aliphatic (preferably alkyl), heteroaliphatic, aryl, heteroaryl or aralkyl.

Ligands are referred to herein as being either 'hydrolysable' or 'non-hydrolysable'. It will be appreciated that a hydrolysable ligand is a ligand reactive to hydrolysis by $H_2O$, and a non-hydrolysable ligand is a ligand stable to hydrolysis by $H_2O$. $H_2O$ acts to supply oxygen to growing metal oxide nanoparticles and to effect cleavage of hydrolysable ligands. The process of the invention involves exposure to $H_2E$, wherein E may be O, S, Se or Te. In the context used herein 'hydrolysable' is intended to mean not only 'reactive to $H_2O$', but also to encompass 'reactive to $H_2E$, wherein E is any of O, S, Se or Te'. Similarly, 'non-hydrolysable' encompasses ligands chemically stable to $H_2E$, wherein E is any of O, S, Se or Te. $H_2E$ acts to supply E to growing nanoparticles and to effect cleavage of hydrolysable ligands. "Hydrolysable" and "non-hydrolysable" ligands may alternatively be referred to as "cleavable" and "non-cleavable", respectively. It will be appreciated that the process of forming nanoparticles may involve reactions other than hydrolysis alone. In the context of this disclosure, the structural definitions as used herein to define ligands falling within these classes are sufficient, in themselves, to determine ligand identity, i.e. of ligand X and $R^a$.

As an alternative to $H_2E$, another agent (e.g. an oxidising agent) may be used to supply oxygen or chalcogen to growing nanoparticles and to effect removal of cleavable ligand $R^a$. Thus, the invention encompasses processes where an oxidising agent is used as an alternative to $H_2E$.

The extent of surface coverage (or surface capping) of nanoparticles by surface-functionalizing ligand X can be expressed as a percentage and may be calculated as described within the examples set out herein.

A chalcogenide is a chemical compound comprising at least one chalcogen atom. In the context used herein a metal chalcogenide refers to a metal sulfide, a metal selenide or a metal telluride.

The term "halogen" or "halide" as used herein means fluoride, chloride, bromide or iodide.

The term "aliphatic" includes both saturated and unsaturated (nonaromatic), straight chain and branched, acyclic, and cyclic (i.e., carbocyclic) hydrocarbons, which are optionally substituted. Aliphatic is intended herein to include, but is not limited to, alkyl, alkenyl, alkynyl, cycloalkyl, cycloalkenyl, and cycloalkynyl moieties, preferably containing from 1 to 25 carbon atoms.

As used herein, an alkyl group is a straight chain or branched, cyclic or acyclic, substituted or unsubstituted saturated group preferably containing from 1 to 25 carbon atoms, from 1 to 20 carbon atoms, from 1 to 18 carbon atoms or from 1 to 12 carbon atoms, inclusive. An alkyl group is preferably a "$C_{1-6}$ alkyl group", that is an alkyl group that is a straight or branched chain with 1 to 6 carbons. The alkyl group therefore has 1, 2, 3, 4, 5 or 6 carbon atoms. Specifically, examples of "$C_{1-6}$ alkyl group" include methyl group, ethyl group, n-propyl group, iso-propyl group, n-butyl group, iso-butyl group, sec-butyl group, tert-butyl group, n-pentyl group, 1,1-dimethylpropyl group, 1,2-dimethylpropyl group, 2,2-dimethylpropyl group, 1-ethylpropyl group, n-hexyl group, 1-ethyl-2-methylpropyl group, 1,1,2-trimethylpropyl group, 1-ethylbutyl group, 1-methylbutyl group, 2-methylbutyl group, 1,1-dimethylbutyl group, 1,2-dimethylbutyl group, 2,2-dimethylbutyl group, 1,3-dimethylbutyl group, 2,3-dimethylbutyl group, 2-ethylbutyl group, 2-methylpentyl group, 3-methylpentyl group and the like. An alkyl group may optionally be substituted.

An alkenyl is as defined above for an alkyl, but including one or more carbon-carbon double bond. An alkynyl is as defined above for an alkyl, but including one or more carbon-carbon triple bonds. An alkenyl or alkynyl group may optionally be substituted.

A heteroaliphatic group is an aliphatic group in which one or more carbon atoms has been replaced by a heteroatoms selected from the group consisting of O, N, S or P, preferably O, N or S. Heteroaliphatic is intended to include heteroalkyl, heteroalkenyl, heteroalkynyl and heterocyclyl (cycloheteroalkyl, cycloheteroalkenyl, and cycloheteroalkynyl moieties). A heteroaliphatic group may optionally be substituted.

An aryl group is a $C_6$-$C_{14}$ aromatic hydrocarbon group comprising one to three rings. Preferably an aryl group is a "$C_{6-10}$ aryl group" and is an aryl group constituted by 6, 7, 8, 9 or 10 carbon atoms. An aryl group includes condensed ring groups such as monocyclic ring group, or bicyclic ring group and the like. Specifically, examples of "$C_{6-10}$ aryl group" include phenyl group, indenyl group, naphthyl group or azulenyl group and the like. It should be noted that condensed rings such as indan and tetrahydro naphthalene are also included in the aryl group. An aryl group includes groups in which an aromatic ring is fused to one or more cycloaliphatic, heterocyclic or heteroaryl rings. An aryl group may optionally be substituted.

A heteroaryl group is an aromatic group comprising one or more rings and having 5 to 14 ring atoms, preferably 5, 6, 9 or 10 ring atoms. Of the ring atoms one or more are carbon and one or more are a heteroatom selected independently from O, S, N and P. A heteroaryl group includes groups in which a heteroaromatic ring is fused to one or more cycloaliphatic, heterocyclic or aryl rings. A heteroaryl group may optionally be substituted.

An aralkyl group is an alkyl moiety substituted with an aryl moiety, both as defined herein.

An alkoxide is a group of formula —OR, wherein R is optionally substituted aliphatic, preferably alkyl.

A thiolate group is a group of formula —SR, wherein R is optionally substituted aliphatic.

An amido group is a group —NRC(O)R or —C(O)NR$_2$, wherein each R is, independently, hydrogen, optionally substituted aliphatic, heteroaliphatic, aryl or heteroaryl.

For the purposes of the present invention, where a moiety is referred to as being optionally substituted, one or more hydrogen atoms of the designated moiety may be replaced by a substituent which results in a chemically feasible compound. Substituents may be independently selected from the group comprising, but not limited to, halide, aliphatic, heteroaliphatic, aryl, heteroaryl, aralkyl, —CN, =O, —OH, —OR$^3$ (e.g. —OMe), —SH, —SR$^3$, nitro, —NH$_2$, —NHR$^3$, —NR$^3_2$, —NHC(O)R$^3$ or —C(O)NH$_2$, —NR$^3$C(O)R$^3$, —C(O)NHR$^3$, —C(O)NR$^3_2$, —C(O)R$^3$ or —OSiR$^3_3$. Further possible substituents include heteroaralkyl, haloaliphatic, haloheteroaliphatic. R$^3$ is optionally substituted aliphatic (preferably alkyl), heteroaliphatic, aryl, heteroaryl or aralkyl. Possible substituents for R$^3$ include halide, aliphatic, heteroaliphatic, aryl, heteroaryl, aralkyl, —CN, =O, —OH, —OR (e.g. —OMe), —SH, —SR, nitro, —NH$_2$, —NHR, —NR$_2$, —NHC(O)R or —C(O)NH$_2$, —NRC(O)R, —C(O)NHR, —C(O)NR$_2$, —C(O)R or —OSiR$_3$. Further possible substituents include heteroaralkyl, haloaliphatic, haloheteroaliphatic. R is aliphatic (preferably alkyl), heteroaliphatic, aryl, heteroaryl or aralkyl.

Where relative reductive stability of ligands is referred to, this can be determined as described within the examples.

A catalyst system as referenced herein is a material, of any physical form, comprising one or more catalytic components.

Whilst the words "comprises" and "comprising" mean "includes among other things", as used throughout they also encompass the option of "consisting essentially of".

In a first aspect, the invention provides a process for the preparation of surface-functionalised metal oxide or metal chalcogenide nanoparticles, the process comprising:
(a) providing a precursor mixture comprising a first organometallic precursor comprising a metal centre M and one or more hydrolysable organic ligands R$^a$, and a source of a non-hydrolysable ligand X, optionally comprising metal centre M, wherein the molar loading, [X]/[M], within the precursor mixture is from 0.001 to 0.4; and (b) reacting the precursor mixture with $H_2E$, wherein E is O, S, Se or Te, to produce surface-functionalised metal oxide or metal chalcogenide nanoparticles.

The process for producing surface-functionalised nanoparticles of the first aspect of the invention enables efficient surface functionalisation without the need for any excess surfactant. The reaction with $H_2E$ of a mixture of organometallic reagent (e.g. $R^a{}_2M$), and an additional, sub-stoichiometric source of a non-hydrolysable ligand X can lead to nanoparticles with full or partial surface coverage of functionalising groups, high crystallinity and good size control.

In the process described above, each $R^a$ may independently be selected from the group consisting of optionally substituted aliphatic, heteroaliphatic, aryl, heteroaryl, aralkyl, amido, alkoxide, aryloxide and thiolate. $R^a$ is preferably optionally substituted $C_{1-6}$ alkyl, more preferably ethyl.

In some embodiments, substituents on $R^a$ may be one or more of the group comprising, but not limited to, halide, aliphatic, heteroaliphatic, aryl, heteroaryl, cyanate, epoxide, amine ($-NH_2$, $-NHR^3$, $-NR^3{}_2$), $-OR^3$ (e.g. $-OMe$), nitro, $-C(O)R^3$ or $-OSiR^3{}_3$ wherein $R^3$ is optionally substituted aliphatic (preferably alkyl), heteroaliphatic, aryl, heteroaryl or aralkyl. Further possible substituents include haloaliphatic, haloheteroaliphatic and heteroaralkyl. Substituents are preferably one or more of halide, aliphatic, heteroaliphatic, aryl, heteroaryl, $-OR^3$ (e.g. $-OMe$), nitro, $-C(O)R^3$ or $-OSiR^3{}_3$ wherein $R^3$ is optionally substituted aliphatic (preferably alkyl), heteroaliphatic, aryl, heteroaryl or aralkyl. Possible substituents on $R^3$ include halide, aliphatic, heteroaliphatic, aryl, heteroaryl, aralkyl, $-CN$, $=O$, $-OH$, $-OR$ (e.g. $-OMe$), $-SH$, $-SR$, nitro, $-NH_2$, $-NHR$, $-NR_2$, $-NHC(O)R$ or $-C(O)NH_2$, $-NRC(O)R$, $-C(O)NHR$, $-C(O)NR_2$, $-C(O)R$ or $-OSiR_3$. Further possible substituents include heteroaralkyl, haloaliphatic, haloheteroaliphatic. R is aliphatic (preferably alkyl), heteroaliphatic, aryl, heteroaryl or aralkyl.

The first organometallic precursor may be homoleptic or heteroleptic, or a mixture thereof. It may be represented by $M(R^a)_n$, wherein n is an integer of one or more. It will be appreciated that the value of n can vary dependent on the identity (oxidation number) of M and the $R^a$ ligands present. For example, where M is zinc, $M(R^a)_n$ could be $MR^a$ with a single bidentate ligand or $M(R^a)_2$ with two $R^a$ ligands which may be the same or different. Thus, examples of the precursor include bis(alkyl)zinc, bis(aryl)zinc, bis(amido) zinc, arylzincalkoxide, aryl zinc aryloxide, arylzincamido, arylzinc thiolates, alkylzinc alkoxide, alkylzinc amido, alkyl zinc thiolates or mixtures thereof. It will be appreciated that zinc in the above listing may be substituted by any other option for M as defined herein, including a mixture of metals.

In any embodiments of the process described above, each X may independently be selected from the group consisting of a carboxylate, a thio-carboxylate, a dithiocarboxylate, a sulphate, a sulfonate, a sulphinate, a phosphonate, a phosphinate, a halide, an amide, a carbonate, a dithiocarbonate and a nitrate. X is preferably a carboxylate or a phosphinate ligand. In certain embodiments, X is a carboxylate of formula $OOCR^b$ or a phosphinate of formula $(O(O)PR^b{}_2)$, wherein each $R^b$ is, independently, optionally substituted aliphatic, heteroaliphatic, aryl or heteroaryl. Preferably, $R^b$ is alkyl, aryl or aralkyl. In some embodiments, $R^b$ is $C_{1-20}$ alkyl (e.g. $C_{5-20}$ alkyl) or phenyl. Exemplary options for ligand X include stearate, benzoate and di(alkyl)phosphinate (e.g. di(octyl)phosphinate). The source of ligand X is may be XH or a second organometallic precursor comprising metal centre M and at least one ligand X (for example, XH, $MX_n$, or a heteroleptic compound comprising metal centre M, at least one ligand X and at least one ligand $R^a$). As described above in respect of $M(R^a)_n$, it will be appreciated that the value of n can vary dependent on the identity (oxidation number) of M and the X ligands present.

In the process of the first aspect of the invention, the precursor mixture comprises a sub-stoichiometric amount of ligand X, in relation to M. The molar loading of ligand X with reference to metal centre M ([X]/[M]) within the precursor mixture is 0.001 to 0.4. In some embodiments the molar loading is from 0.001 to 0.35, preferably 0.001 to 0.33, more preferably 0.001 to 0.25, even more preferably 0.001 to 0.2. In some embodiments, the minimum molar loading is 0.01, preferably 0.05. The molar loading [X]/[M] takes into consideration total M within the precursor mixture, i.e. M provided by the first organometallic precursor and, wherein the source of ligand X comprises M, also the M provided thereby.

Sub-stoichiometric loadings are advantageous in several respects. As the nanoparticle forms, most M atoms/ions are in the crystalline core, and do not bind to any non-hydrolysable ligand. In the case of the preferred, fully crystalline core, the ligand, X, can only bind at the nanoparticle surface. The maximum [X]:[M] thus is defined by the surface to volume ratio of the nanoparticles; ie the fraction of the total M atoms/ions that lie on the surface. This maximum ratio reduces with increasing nanoparticle size, but is always significantly less than equimolar, if a crystalline nanoparticle is to form efficiently. Excess [X] is disadvantageous as it must remain as an unwanted component in a heterogeneous product, for example as $MX_n$, or other unwanted crystal structures, such as organically-modified layered systems. This secondary component is wasteful and introduces additional purification requirements that are particularly incompatible with in situ use in composites. The exact maximum ratio (for a fully saturated surface) will be defined by the nature of X, its coordination to the surface, and its steric bulk, as well as the morphology and crystallography of the core. The dependence of the maximum ratio on nanoparticle size has a useful corollary. Under suitable conditions, the nanoparticles grow to a specific size, selected by the [X]:[M] ratio; once the surface is saturated by [X], further growth is inhibited. Thus size selected growth of nanoparticles is possible. The outcome can be considered a thermodynamic product of the reagents, if ripening is avoided. Alternatively, if nucleation is controlled kinetically (ie initiated rapidly), to generate a fixed, large number of growing nuclei, the nanoparticles will stop growing (before reaching the thermodynamic product size) when the feedstock is exhausted (to give the kinetic product). In this case, the [X]:[M] ratio determines the degree of surface ligand coverage, specified for example, as the percentage of the saturation surface coverage at the size obtained. Well-defined partial surface coverage is a particularly interesting and unique aspect of the invention; it allows stabilisation and dissolution of the nanoparticles whilst maintaining access to the surface for other reagents, for example relevant to catalysis. In summary, sub-stoichiometric ligand concentrations are advantageous in ensuring that fully and partially covered surface-functionalised metal oxide or metal chalcogenide nanoparticles are reliably formed, at controlled size, whilst avoiding the formation of other phases, such as a layered crystal phase or similar.

In some embodiments the metal M is selected from the group consisting of Zn, Al, Ti, Sn, Mg, Ca, Ga, Y, Sc, Zr, Ge, In and lanthanides, or a mixture thereof, preferably Zn. Accordingly, the metal centre M of the first organometallic precursor or the source of ligand X may comprise a mixture of metals. Preferably, the metal M comprises Zn. In some embodiments, metal M is selected from the group consisting of Zn, Al, Ti, Sn, Mg, Ca, Ga, Y, Sc, Zr, Ge, In and lanthanides, or a mixture thereof, and a doping amount of a further metal, such as Ga, Al, Li, Na, K, Cr or a lanthanide, present at <10%, <8%, <6%, <4%, <2% or <1% calculated on the basis of atom % (in metal) in relation to total M in the precursor mixture. In some embodiments, the first organometallic precursor comprises a first component comprising metal centre M and one or more ligands $R^a$ and second component comprising a metal centre different to metal centre M in the first component, such as Ga, Al, Li, Na, K, Cr or a lanthanide, and one or more ligands $R^a$, wherein $R^a$ is as defined herein. The second component may be present at <10%, <8%, <6%, <4%, <2% or <1% calculated on the basis of an atom % (in metal) in relation to total M in the precursor mixture.

Any organic solvent may be used. The solvent should be dry when used to provide the precursor mixture in step (a), until step (b) where $H_2E$ is added.

The precursor mixture may be provided in a non-aqueous solvent. The solvent may be, for example, toluene, hexane, THF, an ether solvent, an amine solvent, squalane, pyridine or acetone.

In some embodiments, the source of non-hydrolysable ligand X is XH or an organometallic compound with metal centre M and one or more ligands X (for example, $MX_2$). Within the precursor mixture ligand exchange occurs to give a heteroleptic organometallic intermediate with at least one ligand $R^a$ and at least one ligand X. The organometallic intermediate can be designated "$R^aMX$". It should be appreciated that "$R^aMX$" is a representative designation. It is not limited to a complex comprising a single metal centre and a single occurrence of $R^a$ and X, but encompasses any coordinating geometry and number of ligands provided at least one of each of M, $R^a$ and X is present.

In an alternative embodiment, the precursor mixture is prepared by adding $M(R^a)_n$ (e.g. $R^a{}_2M$) and a heteroleptic compound comprising metal centre M, at least one ligand X and at least one ligand $R^a$ (e.g. $R^aMX$) to a non-aqueous solvent, for example toluene or hexane.

Step (b) comprises exposing the precursor mixture to $H_2E$. In some embodiments, step (b) comprises adding a solution of $H_2E$ in a solvent, such as a water miscible organic solvent (for example acetone or THF), to the precursor mixture. In some embodiments, where in $H_2E$, E is S, Se or Te, the solvent is an organic solvent in which $H_2E$ gas may be dissolved (e.g. toluene). Preferably, $H_2E$ is added in an amount of 1-1.5 molar equivalent relative to ligand $R^a$ in the precursor mixture. Step (b) may, for example, be carried out at a pressure range of 1-20 bar.

In certain embodiments, step (b) comprises reacting the precursor mixture with $H_2O$. The reaction occurring is a hydrolysis reaction to produce metal oxide nanoparticles. Exposure to $H_2O$ may occur by adding a solution of $H_2O$ with a water miscible solvent or by exposure of the precursor mixture to a humid atmosphere (such as relative humidity of 10% or more). Similarly, exposure to $H_2S$ could occur by adding a solution of $H_2S$ in an organic solvent such as toluene to the precursor mixture.

In some embodiments, the process is carried out under non-basic conditions, i.e. in the absence of any base.

Advantageously, the process may be carried out in the absence of additional or free surfactant within the precursor mixture.

In some embodiments, the process further comprises, after step (b), exposing the surface-functionalised metal oxide or metal chalcogenide nanoparticles to a further organometallic compound comprising a metal centre and one or more hydrolysable organic ligands $R^a$, wherein $R^a$ is as defined herein. The metal centre of the further organometallic compound is preferably different to any metal centre M present in the precursor mixture and may be, for example, Ga, Al, Li, Na, K, Cr or a lanthanide, The further organometallic compound is added at an amount of <10%, <8%, <6%, <4%, <2% or <1% calculated on the basis of atom % (in metal) of its metal centre in relation to total M in the precursor mixture.

Any of the embodiments described herein for the first aspect of the invention may be used in combination mutatis mutandis.

In a second aspect, the invention provides a process for the preparation of a composite material comprising surface-functionalised metal oxide or metal chalcogenide nanoparticles dispersed within a polymeric material, the process comprising:

(a) providing a precursor mixture as defined in respect of the first aspect of the invention and combining the precursor mixture with prepolymer, thermoplastic or curable or cured resin material;

(b) exposing the mixture produced in step (a) to $H_2E$ wherein E is O, S, Se or Te.

In some embodiments, the process comprises removing hydrolysable ligands $R^a$ after step (b). This can be achieved by a variety of purification methods, for example evaporation of volatile ligands.

In some embodiments, the prepolymer comprises a polymerisable or cross-linkable resin, preferably selected from the group consisting of, but not limited to, an epoxy resin, an acrylic resin (e.g. polybutylacrylate), a styrenic resin (e.g. polystyrene), a phenolic resin, an epoxidised phenolic resin, a polyester resin, polycarbonate resin, a phenylenevinylene resin, a fluorene resin, a fluorenevinylene resin, a phenylene resin and a thiophene resin.

In some embodiments, where the precursor mixture is combined with a prepolymer, a cross-linking agent (or hardener) is added to the mixture produced after step (b), and preferably after removal of hydrolysable ligands $R^a$, followed by curing to produce a composite material comprising surface-functionalised metal oxide or metal chalcogenide nanoparticles dispersed within a polymeric material.

In some embodiments, for example where the prepolymer is an epoxy resin, the hardener may be selected from the group consisting of, but not limited to, amines, polyamines, diamines, polyamides, phenolic resins, anhydrides, dianhydrides, isocyanates, diisocyanates and polymercaptans.

Examples of epoxy resins include, but are not limited to, cycloaliphatic epoxy resins, diglycidylether of bisphenol A, bis-(3-glycidyloxy)phenylphosphine oxide, resorcinoldiglycidyl ether, Novolac epoxy resins, diglycidylether of bisphenol F, triglycidylether of triphenylol methane, Triglycidyl p-aminophenol, tetraglycidyl methylene dianiline.

In some embodiments, the thermoplastic may be a thermoplastic selected from the group consisting of, but not limited to, polycarbonates, poystyrenes, polyacrylates, polyesters, polyethers, polyethylenes and polypropylenes.

In some embodiments, the prepolymer may be a curable thermosetting polymer resin (i.e. resin material before curing). Curing can be carried out (according to standard curing procedures e.g. thermal curing) after step (b) to produce a composite material comprising surface-functionalised metal oxide or metal chalcogenide nanoparticles dispersed within a polymeric material.

In some embodiments, X is benzoate and the prepolymer is an epoxy resin.

In some embodiments, where the precursor mixture is combined with a cured resin material, the step of combining comprises soaking the precursor mixture into the cured resin material, optionally with the assistance of a volatile solvent or plasticizer. After step (b) any by-products and solvent could be allowed to diffuse out of the produced composite material.

In some embodiments, where the precursor mixture is combined with a thermoplastic, after exposure to $H_2E$ and removal of hydrolysable ligands, the produced composite material may be subjected to conventional processing, such as melt processing.

In some embodiments, the process is a 'one-pot' process, where all steps are carried out in situ.

In a third aspect, the invention provides surface-functionalised metal oxide or metal chalcogenide nanoparticles, as produced by a process according to the first aspect of the invention.

In a fourth aspect, the invention provides a composite material comprising surface-functionalised metal oxide or metal chalcogenide nanoparticles dispersed within a polymeric material, as produced by the process of the second aspect of the invention.

In a fifth aspect, the invention provides a surface-functionalised metal oxide or metal chalcogenide nanoparticle (or a population thereof), wherein surface functionalisation comprises ligand X as defined herein bound to the nanoparticle. The identity of the metal may be as defined for metal centre M of the first aspect of the invention.

In some embodiments the nanoparticles have a partial surface coverage (i.e. less than 100%, preferably 95% or less) of ligand X covalently bound thereto. In some embodiments, the nanoparticle (or population thereof) has a surface coverage of ligand X bound to the nanoparticle of 1-90%, for example 1-80%. Preferably, the surface coverage is at least 10%. Literature methods for producing surface-functionalised nanoparticles utilise excess free surfactant, which results in the surface of the nanoparticles, in effect, being saturated. In contrast, the present invention provides nanoparticles with partial surface coverage, with the accessible surface being useful for applications in catalysis.

In some embodiments, the nanoparticle (or plurality thereof) comprises metal centre M, wherein the molar loading of ligand X/metal centre M ([X]/[M]) within the nanoparticle (or plurality thereof) is 0.001 to 0.4. In some embodiments the molar loading is from 0.001 to 0.35, preferably 0.001 to 0.33, more preferably 0.001 to 0.25, even more preferably 0.001 to 0.2. In some embodiments, the minimum molar loading is 0.01, preferably 0.05. In some embodiments, metal centre M, as defined in respect of the first aspect of the invention, is selected from the group consisting of Zn, Al, Ti, Sn, Mg, Ca, Ga, Y, Sc, Zr, Ge, In and lanthanides, or a mixture thereof. Preferably, the metal M comprises Zn. In some embodiments, metal M is selected from the group consisting of Zn, Al, Ti, Sn, Mg, Ca, Ga, Y, Sc, Zr, Ge, In and lanthanides, or a mixture thereof, and a doping amount of a further metal, such as Ga, Al, Li, Na, K, Cr or a lanthanide, present at <10%, <8%, <6%, <4%, <2% or <1% calculated on the basis of an atom % (in metal) in relation to total M in the nanoparticle (or plurality thereof).

In some embodiments, the nanoparticles have an average particle size of up to 40 nm, preferably up to 20 nm, more preferably from 2-10 nm (as determined by TEM as described herein). Preferably, in a population of nanoparticles, the standard deviation in particle size is 20% or less, preferably 15% or less.

The nanoparticles of the third and fifth aspects of the invention are useful as a catalyst, for example in the production of methanol from synthesis gas (a mixture of CO, $H_2$ and $CO_2$) or from carbon dioxide and hydrogen mixtures. Accordingly, in a sixth aspect, the invention provides a process for producing methanol from a gas selected from synthesis gas and a carbon dioxide/hydrogen mixture, comprising exposing the gas to nanoparticles of the third or fifth aspect of the invention.

The nanoparticles are advantageous because they can easily be dissolved in a range of solvents (including organic solvents, such as alkane solvents) to produce colloidal solutions of nanoparticles. A colloidal solution is a colloid stabilised such that it is thermodynamically favourable for the nanoparticles to disperse/dissolve in the solvent. Partial surface capping of nanoparticles advantageous as it allows binding of the substrates on the surface of the zinc oxide nanoparticles, an important step in the catalytic cycle and one which is hindered by having a fully capped nanoparticle surface. The use of surface capping ligands is also advantageous because it solubilises the nanoparticles, thereby increasing available surface area (vs. heterogeneous catalysts) and enabling the catalysis to occur in solutions. The capping ligands, further, prevent the aggregation of the nanoparticles which is advantageous because it is known that maximising catalyst surface area correlates with high activity and selectivity. Accordingly, in a preferred embodiment the process of the sixth aspect of the invention comprises preparing a mixture of surface-functionalised nanoparticles of the third or fifth aspect of the invention in an organic solvent and passing a gas selected from synthesis gas and a carbon dioxide/hydrogen mixture through the mixture, preferably wherein the mixture is a colloidal solution or a suspension. The mixture may comprise some proportion of nanoparticles in suspension in addition to colloidal nanoparticles.

In some embodiments, catalysis is achieved using a mixture of surface-functionalised nanoparticles of the third or fifth aspect of the invention with a co-catalyst. for example copper nanoparticles. In some embodiments, the co-catalyst comprises a co-catalyst selected from the group consisting of a metal oxide or mixture of metal oxides, metal nanoparticles, an organic/organometallic complex, a metal hydride, or a mixture thereof (e.g Stryker reagent/cuprous hydride/lithium aluminium hydride). Preferably, the mixture (e.g. colloidal solution) comprises a mixture of surface-functionalised nanoparticles of the third or fifth aspects of the invention and copper nanoparticles. This may be an equimolar mixture.

In some embodiments, wherein the co-catalyst comprises a metal oxide or mixture of metal oxides, the metal therein may be a group 1 metal, a group 2 metal, a group 13 metal, a lanthanide or a first row transition metal. In some embodiments, wherein the co-catalyst comprises metal nanoparticles, the metal nanoparticles may be transition metal nanoparticles. The transition metal is preferably stable to a reducing environment (hydrogen, for example as in a reactor described in the examples herein). Preferably, the transition metal is copper. In some embodiments, wherein the co-catalyst comprises metal nanoparticles (such as copper nanoparticles), the metal nanoparticles are surface-functionalised metal nanoparticles comprising ligand bound to the metal nanoparticles, wherein ligand is selected from the group consisting of a carboxylate, a thio-carboxylate, a dithiocarboxylate, a sulphate, a sulfonate, a sulphinate, a phosphonate, a phosphinate, a halide, an amide, a carbonate, a dithiocarbonate, an amine or and a nitrate ligand, or a mixture thereof. The identity of the ligand may be as defined herein for any of the embodiments of ligand X. In some embodiments, the mixture of surface-functionalised nanoparticles of the second or fifth aspect of the invention and co-catalyst metal nanoparticles comprises a ratio of metal oxide or metal chalcogenide to metal of the metal nanoparticles (e.g. copper) of about 5:95 to 95:5, about 20:80 to 80:20, about 25:75 to 75:25, about 40:60 to 75:25, about 50:50 to 70:30, about 60:40 to 70:30, or about 65:35, wherein the ratio is a weight ratio of the metal oxide or metal chalcogenide to the metal of the metal nanoparticles (e.g. ZnO:Cu). Accordingly, in some embodiments, the process of the sixth aspect of the invention comprises: preparing a catalytic material by mixing nanoparticles of the third or fifth aspects of the invention with metal nanoparticles in an organic solvent to provide a catalytic material, and exposing the gas to the catalytic material, wherein the metal nanoparticles are surface-functionalised metal nanoparticles comprising ligand bound to the metal nanoparticles, wherein ligand is selected from the group consisting of a carboxylate, a thio-carboxylate, a dithiocarboxylate, a sulphate, a sulfonate, a sulphinate, a phosphonate, a phosphinate, a halide, an amide, a carbonate, a dithiocarbonate, an amine and a nitrate ligand, or a mixture thereof. The identity of the ligand may be as defined herein for any of the embodiments of ligand X.

In a seventh aspect, the invention provides a catalyst comprising nanoparticles of the third or fifth aspect of the invention.

In an eighth aspect, the invention provides a catalyst system comprising nanoparticles of the third or fifth aspect of the invention and a co-catalyst. In some embodiments, the co-catalyst is selected from the group consisting of a metal oxide or mixture of metal oxides, metal nanoparticles (for example copper nanoparticles), an organic/organometallic complex, a metal hydride, or a mixture thereof (e.g Stryker reagent/cuprous hydride/lithium aluminium hydride). In some embodiments, wherein the co-catalyst comprises metal nanoparticles (such as copper nanoparticles), the metal nanoparticles are surface-functionalised metal nanoparticles comprising ligand bound to the metal nanoparticles, wherein ligand is selected from the group consisting of a carboxylate, a thio-carboxylate, a dithiocarboxylate, a sulphate, a sulfonate, a sulphinate, a phosphonate, a phosphinate, a halide, an amide, a carbonate, a dithiocarbonate, an amine and a nitrate ligand, or a mixture thereof. Embodiments of the co-catalyst as defined in respect of the sixth aspect of the invention apply equally to the eighth aspect of the invention. The identity of the ligand may be as defined herein for any of the embodiments of ligand X. In some embodiments, the ratio of metal oxide or metal chalcogenide to metal of the metal nanoparticles (e.g. copper) of about 5:95 to 95:5, about 20:80 to 80:20, about 25:75 to 75:25, about 40:60 to 75:25, about 50:50 to 70:30, about 60:40 to 70:30, or about 65:35, wherein the ratio is a weight ratio of the metal oxide or metal chalcogenide to the metal of the metal nanoparticles (e.g. ZnO:Cu).

In a ninth aspect, the invention provides a process for producing a catalyst system, the process comprising providing surface-functionalised metal oxide or metal chalcogenide nanoparticles of the third of fifth aspects of the invention and mixing said nanoparticles with metal nanoparticles in a solvent, preferably an organic solvent. In some embodiments, the metal nanoparticles are copper nanoparticles. In some embodiments, the metal nanoparticles (e.g. copper nanoparticles) are surface-functionalised nanoparticles comprising ligand bound to the nanoparticles, wherein ligand is selected from the group consisting of a carboxylate, a thio-carboxylate, a dithiocarboxylate, a sulphate, a sulfonate, a sulphinate, a phosphonate, a phosphinate, a halide, an amide, a carbonate, a dithiocarbonate, an amine and a nitrate ligand, or a mixture thereof. The identity of the ligand may be as defined herein for any of the embodiments of ligand X.

In some embodiments, ligand X present on the metal oxide or metal chalcogenide nanoparticles is more reductively stable than the ligand of the surface-functionalised metal nanoparticles. In some embodiments, ligand X is a phosphinate ligand and the ligand of the surface-functionalised metal nanoparticles is a carboxylate ligand. In some embodiments, a ligand comprises a phosphinate is a di(alkyl)phosphinate, for example a di($C_{5-20}$alkyl)phosphinate such as di(octyl)phosphinate. In some embodiments, a carboxylate is COCR$^b$, wherein R$^b$ is alkyl, for example $C_{5-20}$ alkyl.

In a tenth aspect, the invention provides a catalyst system as produced by the process of the ninth aspect of the invention.

In an eleventh aspect, the invention provides a composite material comprising a plurality of nanoparticles of the third or fifth aspect of the invention and a polymeric material, preferably wherein the nanoparticles are dispersed within the polymeric material. In some embodiments, the polymeric material is a thermoplastic or resin which may be as defined in any of the embodiments of the second aspect of the invention or a polymer formed from a pre-polymer as defined in the second aspect of the invention.

Preferred features of the first aspect of the invention also apply to the second, third, fourth, fifth, sixth, seventh, eighth, ninth, tenth and eleventh aspects mutatis mutandis.

EXAMPLES

All reactions involving air-sensitive reagents were conducted under a nitrogen atmosphere using either standard Schlenk techniques or in a nitrogen-filled glovebox.

Materials

Unless otherwise stated, solvents were freshly degassed prior to use by performing at least three freeze-pump-thaw cycles. Diethylzinc was purchased from Aldrich, vacuum distilled and stored in an ampoule, under nitrogen, at −38° C. The epoxy resin system used was produced by Huntsman Advanced Materials, and consisted of a diglycidyl ether of bisphenol A (DGEBA) and an amine hardener, thermally cured. The DGEBA resin (CY219), was donated by Moldlife Ltd. The hardener (XB3473) was purchased from Robnor Resins. The composites were cured in silicone moulds, prepared using Elastosil M4641 (Amber Composites) Parts A and B.

Zinc bis(dodecanoate), and zinc bis(hexanoate) were prepared according to the method described by Berkesi et al. *Inorg. Chim. Acta,* 1992, 195, 169-173, from reaction of the respective acid with Zn(OH)$_2$ in boiling octane. Zinc bis(stearate) was prepared by the method described by Ekwunife et al., *Journal of the Chemical Society: Faraday trans-* actions I, 1975, 71, 1432-1446 from reaction of in situ prepared potassium stearate with zinc chloride in an ethanol solution.

Instrumentation

Infra-red (IR) spectroscopy was carried out using a Perkin Elmer Spectrum 100 Fourier Transform IR spectrometer: powder samples were analysed using the Attenuated Total Reflection (ATR) accessory.

Thermogravimetric analysis (TGA) was carried out using a Perkin Elmer Pyris 1 TGA machine, under a flow of dry air, from 50 to 800° C., at a heating rate of 10° C./min.

Optical absorption spectra were collected on a Perkin Elmer Lambda 950 spectrophotometer using toluene as the solvent and a nanoparticle concentration of 10 $\mu gmL^{-1}$. Photoluminescence measurements were carried out using a CaryEclipse spectrometer, using chloroform as the solvent and a nanoparticle concentration of 1 $gmL^{-1}$.

High-resolution Transmission Electron Microscopy (HR-TEM) was carried out using a JEOL 2010 microscope. Nanoparticle samples were drop-cast ($CHCl_3$ solution) onto 300-mesh, holey carbon-coated copper films (Agar Scientific) and imaged at an operating voltage of 200 kV. Thin slices (~90 nm thick) of nanocomposite samples were cut using a diamond knife microtome, placed directly onto 300-mesh copper films (Agar Scientific) and imaged at an operating voltage of 100 kV. Digital images were analysed for particle sizing using the software ImageJ, version 1.40 g (W. Rasband, National Institute of Health); particles were measured manually.

X-ray Diffractometry (XRD) was performed using an X'Pert Pro diffractometer (PANalytical B. V, The Netherlands) and X'Pert Data Collector software, version 2.2b. The instrument was used in the theta/theta reflection mode, fitted with a nickel filter, 0.04 radian Soller slit, 10 mm mask, ¼° fixed divergence slit, and ½ ° fixed antiscatter slit. Samples were analysed with a step size of 0.0041778°, at a scanning speed of 0.027852° $s^{-1}$. The diffraction patterns were analysed using Fityk (version 0.9.0; Marcin Wojdyr, 2010): the peaks were fitted to a Pseudo-Voigt function using the Levenberg-Marquardt algorithm and the particle size was calculated using the fitted full-width half-maximum.

Example 1

Zinc Oxide Nanoparticle Synthesis

Two precursor stock solutions were prepared: (A) 1.0 M $ZnEt_2$ in toluene; (B) 1.0 M [Zn] in toluene.

Stock solution B was prepared by mixing $ZnEt_2$ and $Zn(OOCR)_2$ in toluene in the appropriate ratio to give a carboxylate loading [OOCR]/[Zn] of 0.20 or 0.33, and equilibrating for 2-4 h (OOCR=hexanoate and dodecanoate) or 16 h (OOCR=stearate). The hexanoate and dodecanoate solutions were clear after 2 h; the stearate solutions required gentle heating to achieve full dissolution. After the equilibration period, the solutions were made up to volume using a volumetric flask.

A precursor mixture was then formed by mixing proportions of each stock solution and making up to the correct volume with the appropriate solvent in an inert atmosphere glovebox (hexane or toluene). In general, nanoparticle precursor solutions were made up to a volume such that the total concentration of zinc species in the precursor mixture was 0.15 M. For the rapid hydrolysis method, as described below, the total concentration of zinc species was 0.15 M after the addition of the water solution.

For both types of nanoparticle synthesis, after the required reaction time, the particles were precipitated using excess acetone, centrifuged (10000 rpm.; 15 min) and the liquid decanted. The particles were washed by re-suspending in a small amount of fresh toluene and re-precipitating with excess acetone. Centrifugation was repeated and the wet product paste dried in vacuo for 16 h.

Rapid Hydrolysis Method

A solution of distilled water in HPLC grade acetone (0.86 M, 2.30 mL, 1.98 mmol $H_2O$) was added dropwise to the precursor mixture (total addition time 4 min); a gel stage was observed after approximately 75% of the water solution was added, lasting 5-10 seconds. The solution was stirred for a further 2 h.

Slow Hydrolysis Method

In order to maintain a constant, reproducible humidity atmosphere and to minimise solvent loss during the experiment, the samples were placed into a glass tank which had been equilibrated for at least 18 h with a saturated salt solution and the lid was sealed with vacuum grease. Two relative humidities were chosen: 32% ($CaCl_2.6H_2O$) and 11% (LiCl). The humidity was verified with a digital hygrometer during equilibration and was found not to change during removal and replacement of the lid. The reactions were carried out at 20±2° C. which corresponds to a change in absolute humidity of ±0.5 $gm^{-3}$ (±0.02 $mmoldm^{-3}$) for the 32% solution and ±0.2 $gm^{-3}$ (±0.01 $mmoldm^{-3}$) for the 11% solution, which was considered negligible.

The precursor solutions were prepared and sealed in vials. The vials were brought out of the glovebox, the lids removed, and the vials placed in the controlled humidity chamber. The solutions were allowed to equilibrate for 15 min before stirring for a further 24 h. No gel stage was observed.

Surface-modified nanoparticles were prepared at carboxylate loadings, [OOCR]/[Zn], of 0.05 to 0.33 using both the rapid hydrolysis and slow hydrolysis methods. Non-modified nanoparticles were also prepared as a control. The relative proportions of stock solutions A and B and solvent used in preparation of the precursor solutions are shown in Table 1.

TABLE 1

| [OOCR]/ | Stock solution/mL | | Solvent/mL | | $[Zn]^1$/ | [Et]/ |
|---|---|---|---|---|---|---|
| [Zn] | A | B | Rapid hydrolysis | Slow hydrolysis | M | M |
| 0.33 | — | 1.00 | 3.4 | 5.7 | 0.15 | 0.25 |
| 0.20 | 0.40 | 0.60 | | | | 0.27 |
| 0.14 | 0.57 | 0.43 | | | | 0.28 |
| 0.10 | 0.70 | 0.30 | | | | 0.28 |
| 0.07 | 0.80 | 0.20 | | | | 0.29 |
| 0.05 | 0.85 | 0.15 | | | | 0.29 |
| 0.00 | 1.00 | — | | | | 0.30 |

$^1$total concentration of zinc after addition of water (for rapid hydrolysis)

In the absence of carboxylate ([$OOCR^a$]/[Zn]=0), an opaque nanoparticle suspension was formed that precipitated instantly when stirring was discontinued. The particles could be re-suspended in chloroform by sonication and were found to be largely agglomerated, forming aggregates on the order of 50 nm-2 μm, by TEM. Regions between the particles had an appearance similar to that of sintered particles, indicating that the particles had aggregated and become permanently fused during synthesis. The formation of agglomerated particles in the absence of carboxylate (and where no excess or free surfactant is used) is a problem addressed by the invention.

Characterisation of Stearate-Functionalised Nanoparticles Formed by Rapid Hydrolysis Method The surface-functionalised nanoparticle synthesis conditions utilised a precursor ratio of diethylzinc to zinc bis (stearate) (ZnSA$_2$) of 9:1, in toluene, resulting in a carboxylate loading, [OOCR$^a$]/[Zn], of 0.2 (R$^a$=(CH$_2$)$_{16}$CH$_3$; n=0.11 in Scheme 1).

Scheme 1. A general form of the nanoparticle snythesis where the source of X is MX$_2$

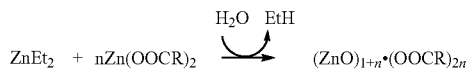

Figure 2:
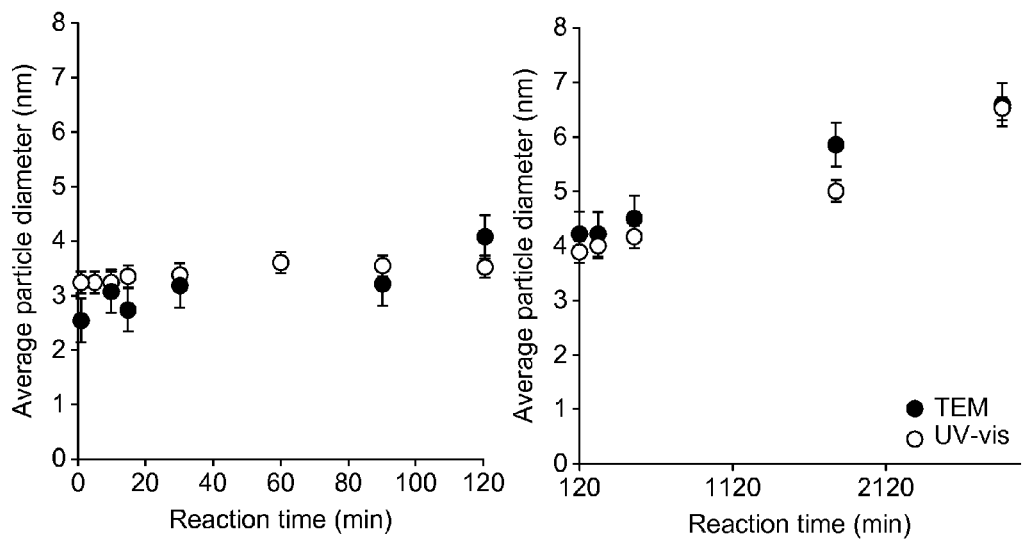
FIG. 2 shows plots of the average particle size (measured by UV-vis spectroscopy and TEM) over time for ZnO particles prepared with a stearate loading of [SA]/[Zn]=0.2. The error bars shown are representative of the standard deviation measured for 10 trials of the 2 h timepoint.

ZnEt$_2$ + nZn(OOCR)$_2$ $\xrightarrow{\text{H}_2\text{O \quad EtH}}$ (ZnO)$_{1+n}$•(OOCR)$_{2n}$ The functionalised nanoparticles formed rapidly and remained stably dispersed, at a consistent size (as assessed by TEM, UV/vis), in the reaction growth mixture, for several hours (FIG. 2). The resulting nanoparticle suspensions (typical reaction 2 h) could be reversibly dissolved and precipitated on addition of excess toluene and acetone, respectively. Once isolated and dried, the particles formed a free-flowing powder (89% yield) that could be easily re-dissolved in toluene or chloroform by gentle heating, to form clear solutions. Toluene solutions (1 mgmL$^{-1}$) precipitated a white film after standing for two days, but the film was easily re-dissolved on heating. Non-functionalised particles ([OOCR$^a$]/[Zn]=0) were found to increase in size on heating the dried powder to 100° C. for 6 hours (average crystallite size increase from 4 nm to 10 nm, as determined by XRD). In contrast, the carboxylate-functionalised particles showed no change in size, morphology, or dispersibility on heating, demonstrating the stability imparted by surface-functionalisation.

XRD analysis (FIG. 3(a)) of the nanoparticles confirmed the formation of crystalline ZnO (wurtzite) with extra, broad peaks at low angle due to the organic component (vide infra). TEM showed the particles to be roughly spherical, non-agglomerated, and nearly monodisperse, with a narrow size-distribution (standard deviation, σ=15%, FIG. 3(c)). The average size of the particles was estimated from the XRD pattern using the Scherrer equation (B. D. Cullity, Elements of X-ray Diffraction, 2nd ed., Addison-Wesley, 1978), and from the UV-vis absorption spectrum using the relation derived by Meulenkamp and described below. The measured particle size was very reproducibly 3-4 nm with excellent agreement between the size measurement techniques (mean of 10 independent syntheses was 3.6±0.4 nm by TEM, 3.1±0.4 nm by XRD, and 3.6±0.2 nm by UV-Vis spectroscopy).

Infra-red (IR) spectroscopy confirmed the presence of carboxylate groups; the carboxylate antisymmetric and symmetric vibrational modes were broadened and shifted compared to ZnSA$_2$, at 1550 and 1418 cm$^{-1}$, respectively (1537 and 1398 cm$^{-1}$, respectively for ZnSA$_2$). The difference, A, between the two modes, 132 cm$^{-1}$, indicates that the stearate groups adopt a bridging arrangement on the nanoparticle surface (as illustrated in FIG. 1). The presence of a high carboxylate content in the TGA and IR analyses, combined with the solubility of the nanoparticles in organic solvents, was taken as good evidence for surface-functionalisation. A broad, weak absorption centred at approximately 3400 cm$^{-1}$ was also present in the IR spectrum, which may be due either to small amounts of residual moisture or to additional surface functionalisation with —OH groups.

For a constant carboxylate loading of 0.2, decreasing the carboxylate alkyl chain length suggested a slight increase in average particle size (stearate, dodecanoate, hexanoate; average size=3.6±0.2, 3.9±0.4, and 4.1±0.4 nm, respectively, as assessed by TEM), and no change in particle morphology was observed. TGA indicated a significant organic content, reducing with chain length, as expected (38, 32, and 20 wt % for stearate, dodecanoate, and hexanoate respectively; expected content 41, 33, and 22 wt %, respectively). The percentage organic component was used to calculate the surface coverage (surface area capped by carboxylate ligands) based on the measured average particle size, according to the calculation described below. The calculated surface coverage was above 80% for each alkyl chain length investigated.

Figure 4:
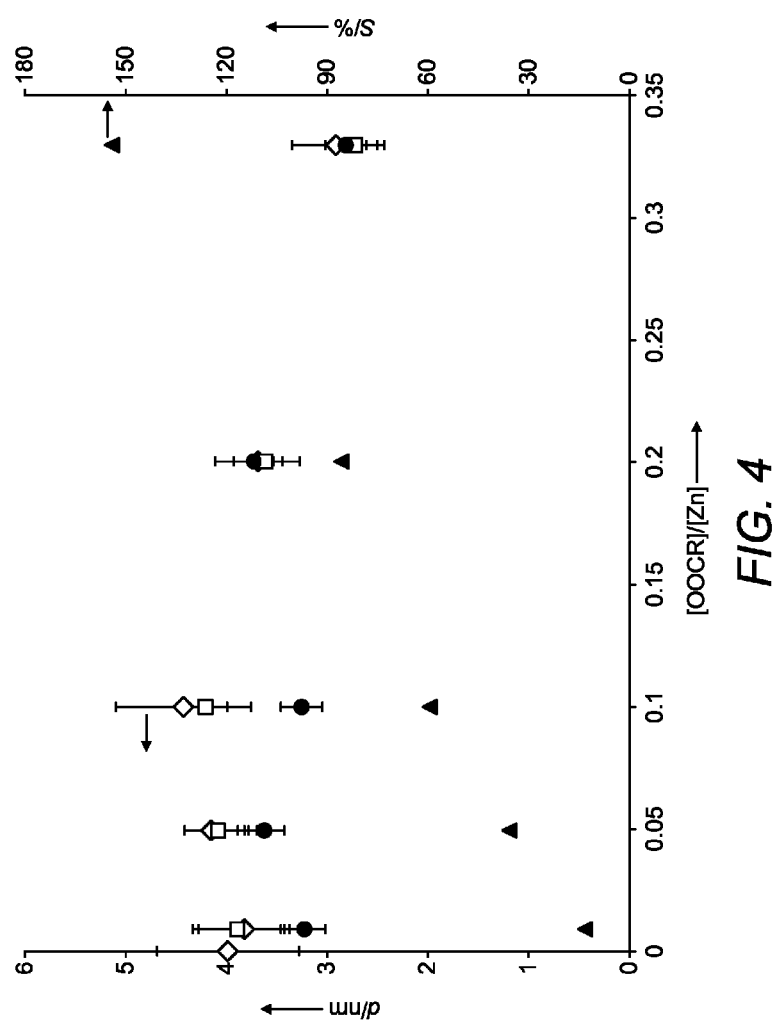
FIG. 4 shows a plot of the average particle diameter (d), measured by TEM (squares), XRD (diamonds), and UV-vis spectroscopy (circles), and calculated surface coverage (S; gray triangles) for ZnO nanoparticles prepared with varying carboxylate loadings. The error bars shown represent the standard deviation for multiple repeat reactions; calculated error bars for S are smaller than the data points as shown (±2%).

For the standard synthesis conditions, particle size was found to be largely independent of carboxylate loading: the overall size change was less than 1 nm (FIG. 4).

Figure 5:
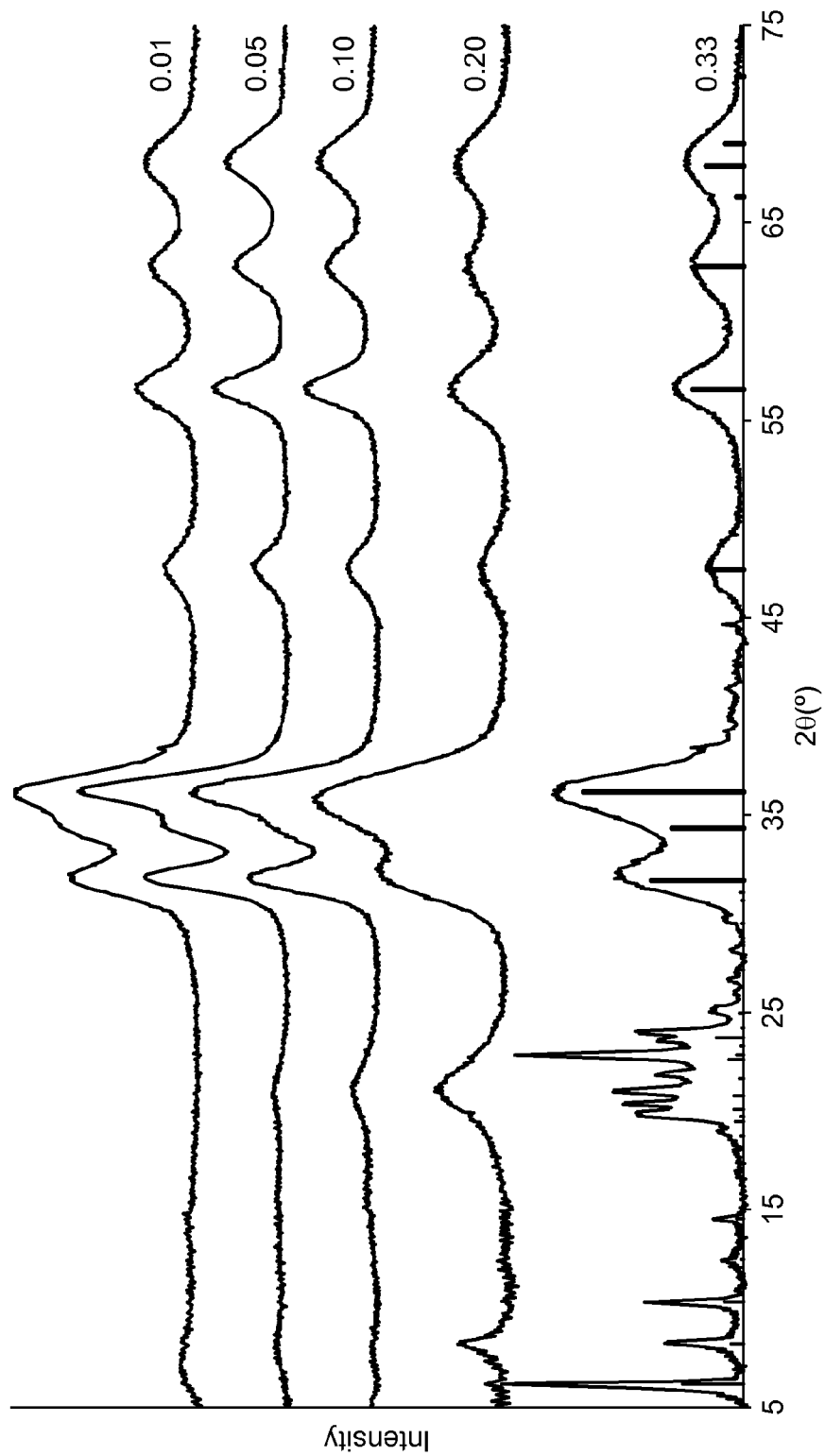
FIG. 5 shows X-ray patterns for ZnO nanoparticles prepared with varying stearate (R=$(CH_2)_{16}CH_3$) loading, [OOCR]/[Zn]. ZnO reference lines (black) and zinc bis (stearate) (grey) (ICPDF4+ database, PDF no. 36-1451 and 55-1618, respectively).
Figure 6:
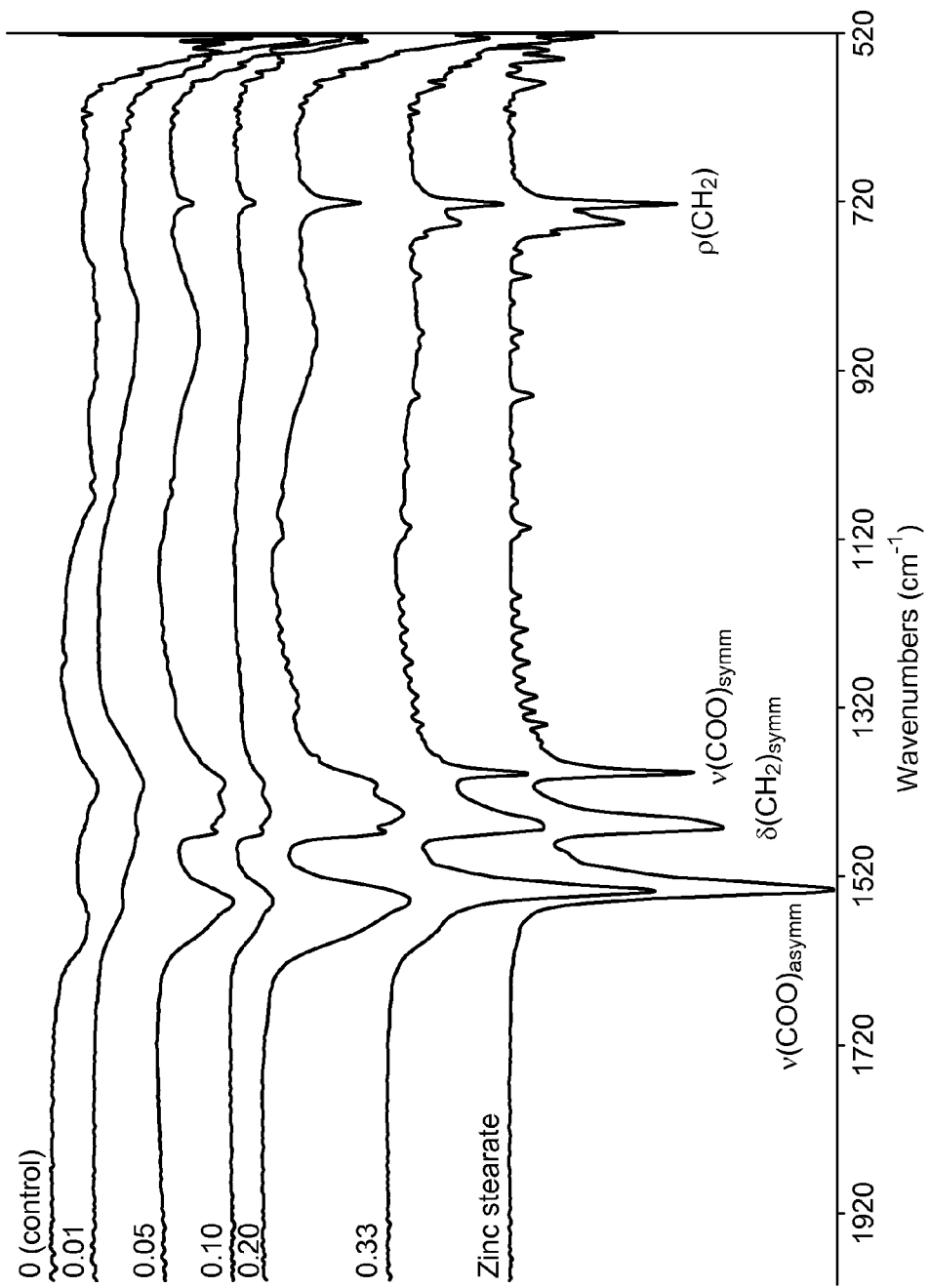
FIG. 6 shows an infra-red spectra for ZnO nanoparticles with varying stearate loadings, compared to zinc bis(stearate). "ν" refers to a stretching mode, "δ" refers to a bending mode, and "ρ" refers to a rocking mode.

Carboxylate loading can be used to adjust the degree of surface coverage. The total carboxylate content (calculated by TGA) matched the intended loading for each sample which, based on the measured average particle size, corresponds to a decrease in surface coverage with decreasing loading (FIG. 4). The calculated coverage for the 0.33 loading sample was greater than 100% (154%), a result that can be attributed to the presence of excess Zn(SA)$_2$. Indeed, XRD (FIG. 5) showed crystalline ZnO (wurtzite) for all carboxylate loadings, but at the highest loading of carboxylate (sample a, [SA]/[Zn]=0.33) distinctive sharp peaks matching ZnSA$_2$, were also present between 5-25° 2θ. Diffuse peaks between 18-28°, associated with lateral chain packing, appear gradually as surface coverage increases and the stearate chains become more ordered. The IR spectrum matched that of ZnSA$_2$ (FIG. 6) supporting the XRD assignment. The IR carboxylate absorbances broadened and shifted to higher frequency with decreasing carboxylate loading, suggesting that the predominant form of the stearate groups in these samples was a bound, bridging state on the nanoparticle surfaces, rather than as Zn(SA)$_2$. Qualitatively, dispersibility of the dried nanoparticles decreased with decreasing carboxylate content, correlating with the proposed decrease in surface coverage. It can be concluded that, for the rapid hydrolysis process, the particle size is primarily determined by the nucleation step (number of nuclei formed); the particles grow to 3-4 nm with the carboxylate groups being either distributed over the surfaces to give a (partial) surface coverage ([OOCR]/[Zn]≤0.2) or segregated into fully capped nanoparticles and excess Zn(OOCR)$_2$ ([OOCR]/[Zn]>0.2). The ability to systematically control surface coverage is useful for many applications where surface access is important, such as catalysis.

Figure 7:
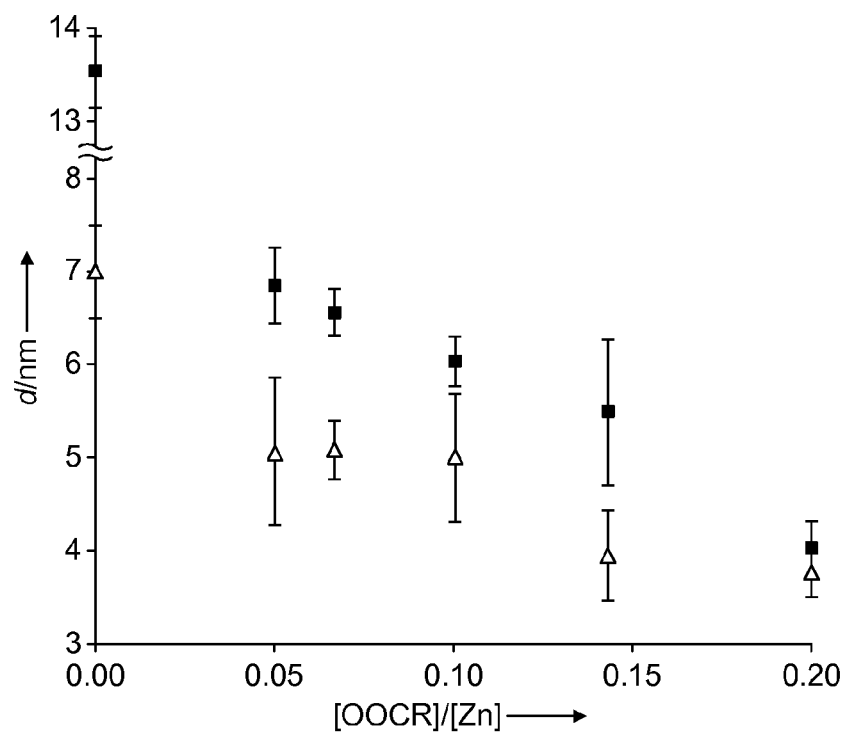
FIG. 7 shows the effect of carboxylate loading and relative humidity on the average particle diameter (d) of ZnO nanoparticles prepared by the slow hydrolysis method (measured by XRD); triangles: 32% RH, squares: 11% RH. The error bars represent the standard error in the mean for multiple repeat reactions of each data point. Unlike the rapid hydrolysis experiments, the particle size was independent of solvent and carboxylate alkyl chain length (within error) and the Figure therefore collates all data collected.

Characterisation of Stearate-Functionalised Nanoparticles Formed by Slow Hydrolysis Method When the hydrolysis rate is slowed down, by allowing the water to diffuse in from a vapour of controlled humidity, particle size is dependent on carboxylate loading (FIG. 7). For a carboxylate loading of 0.2, soluble, largely spherical, 4 nm nanoparticles were obtained. Unlike the rapid hydrolysis experiments, the particle size was independent of carboxylate alkyl chain length. However, at lower carboxylate loadings, particle size increased, consistent with growth limited by carboxylate termination rather than nucleation.

Calculation of Particle Size by UV-Vis Spectroscopy

The approximation empirically derived by Meulenkamp was used to estimate particle size (E. A. Meulenkamp, J.

*Phys. Chem. B.*, 1998, 102, 5566-5572). The wavelength at which the absorption was at half the maximum value, $\lambda_{1/2}$, was related to the particle diameter, d, by:

$$\frac{1240}{\lambda_{1/2}} = 3.556 + \frac{799.9}{d^2} - \frac{22.64}{d} \quad (6)$$

Equation 6 is valid for particle diameters between 2.5 and 6.5 nm. The value of $\lambda_{1/2}$ was estimated as the maximum in the derivative of the absorption spectrum for each sample, which is expected to deviate from the true $\lambda_{1/2}$ by less than 1 nm.

Calculation of Particle Surface Coverage by Thermogravimetric Analysis (TGA)

The theoretical total surface area ($S_T$) of nanoparticles in a sample is given as:

$$S_T = S_p \times N_p \quad (1)$$

where $S_p$ is the surface area per particle and $N_p$ is the total number of particles, given by:

$$N_p = \frac{nV_m}{V_p} \quad (2)$$

where n is the number of moles of ZnO, $V_m$ is the molar volume of ZnO ($1.4353 \times 10^{25}$ Å$^3$ mol$^{-1}$) and $V_p$ is the volume per particle. Assuming that the particles are perfect spheres, rearranging equations 1 and 2 gives:

$$\frac{S_T}{S_p} = \frac{nV_m}{V_p} \bigg| \frac{S_T}{4\pi r^2} = \frac{nV_m}{\left(\frac{4}{3}\pi r^3\right)} \rightarrow S_T = \frac{3nV_m}{r} \quad (3)$$

where r is the radius of the particles (average of measurements by HR-TEM, UV-vis, and XRD analysis).

The number of moles of carboxylate per mole of ZnO, $n_c$, for each sample was calculated from the organic content measured by TGA:

$$n_c = \frac{(W_o/M_c)}{(W_i/81.39)} \quad (4)$$

where $W_o$, $W_i$ are the weight percent (wt %) or organic and inorganic components, respectively, and $M_c$ is the molecular weight of the carboxylate.

The surface area per carboxylate molecule was estimated as 20 Å$^2$, based on reported areas for self-assembled carboxylate monolayers (Shaitan et al, *Biophysics*, 1999, 44, 429-434 and Husbands et al, *Powder Technol.*, 1971, 5, 31-38). The theoretical surface area that could be occupied by carboxylate groups, $S_s$, was then calculated as:

$$S_S = Z \times n_c \times 20 \text{ Å}^2 \quad (2)$$

where Z is Avogadro's number, and $n_c$ is the number of moles of carboxylate (calculated from the total organic content). The ratio of $S_S$ to $S_T$ gives the percentage coverage.

In the above equation, the ZnO molar volume and formula mass can be substituted for that of the metal chalcogenide of choice.

It is also possible to determine whether or not a nanoparticle has partial surface coverage by preparing a series of samples at different ratios. At some point, excess ligand precipitates and is visible in the XRD or washed out during purification, allowing determination of the 100% surface coverage ratio. As this point, you have the organic loading for a dense layer on a known surface area (since you know the size). Partial coverage can be assessed relative to this value and it is possible to determine whether a particle has complete surface coverage or partial surface coverage. For example, excess ligand is visible in the XRD in FIG. 5 at 0.33 loading.

Example 2

Nanocomposite Synthesis

To demonstrate the compatibility of the described process with cross-linking resins, in situ ZnO/epoxy resin nanocomposites were prepared. A zinc precursor mixture with carboxylate loading of 0.2 was added to an epoxy prepolymer of the diglycidyl ether of bisphenol A (DGEBA) and hydrolysed. The volatile compounds were removed and the ZnO/epoxy pre-polymer was mixed with an amine hardener, before casting and curing.

Nanocomposites were synthesised by addition of organometallic zinc precursor solutions to an epoxy prepolymer (DGEBA). The epoxy prepolymer (DGEBA) was dried under vacuum at 65° C. for 6 hours prior to addition of the organometallic zinc precursor solution. Syntheses were carried out with an "uncapped" precursor solution (ZnEt$_2$) as a control, and with solutions with a carboxylate loading, [OOCR]/[Zn], of 0.2. The ZnEt$_2$/"EtZn(OOCR)" precursor solutions were equilibrated for 18 hours prior to use, and both the stearate and benzoate derivatives gave clear solutions after gentle heating. Reagent quantities are shown in Table 2.

The precursor solution was added to the dried DGEBA and stirred to form a homogeneous solution. A solution of distilled water (2 equiv.) in acetone (2-4 mL) was added dropwise and the mixture stirred for 2 h. Volatiles were removed in vacuo for 10 min at 25° C. and a further 30 min at 65° C. Hardener was then added, mixed well, the mixture degassed at 65° C. for 15 min, and transferred to the moulds. The DGEBA/ZnO/hardener mixture (100:23 DGEBA:hardener, by weight) was degassed in the moulds by heating to 100° C. under vacuum, then cured by heating under air at 120° C. for 2 h and 140° C. for 2 h.

TABLE 2

Reagent quantities and TGA results for nanocomposites

| Capping agent | Precursor mixture | | | | Measured | |
|---|---|---|---|---|---|---|
| | Epoxy/ g | Hardener/ g | ZnEt$_2$/ mmol[a] | XA/ mmol[b] | content/ wt % | Vol % |
| Stearate | 7.961 | 1.842 | 5.94 | 0.68 | 5.3 | 1.1 |
| Benzoate | 4.057 | 0.933 | 4.76 | 1.00 | 6.4 | 1.4 |

[a]1M solution in toluene.
[b]for stearate-capped, XA = ZnSA$_2$; for benzoate-capped, XA = benzoic acid.

When stearate-functionalised ZnO nanocomposites were prepared and observed by TEM, some agglomerated regions of nanoparticles formed. Although both the stearate-capped nanoparticles and the epoxy pre-polymer are soluble in toluene, they phase segregate on curing. Although the particles were agglomerated, they were separated from one another (not permanently fused), indicating segregation due to the surface-modifying alkyl chains. When the functionalizing ligand was benzoate, well-dispersed and well-distributed ZnO nanoparticles were formed. The nanoparticle sizes were measured to be 3-4 nm, in good agreement with the other nanoparticles synthesised using this method. It is proposed that the use of the aromatic benzyl group improves compatibility between the epoxy pre-polymer (which has aromatic functionality in the polymer chain) and the surface capping groups on the zinc oxide nanoparticles, thus improving dispersion quality in the nanocomposite.

Example 3

Synthesis of Phosphinate Capped ZnO Nanoparticles 500 mg of di-octyl phosphinic acid was dried under vacuum for an hour and dissolved in 57.5 ml of dry toluene with 1.06 g of $ZnEt_2$ (5 equiv) and left to stir overnight. 0.310 ml of distilled water (10 equiv) in a 0.4M solution in acetone was added dropwise over 20 minutes with heavy stirring, the solution went from colourless to yellow to a thick gel before forming a cloudy suspension. The suspension was stirred for a further two hours. The stirring was stopped the white precipitate settled on the bottom, this was transferred to centrifuge tubes and mixed with acetone (1:1), the samples were centrifuged at 3900 rpm for 20 minutes, the liquid was decanted and the solids were re-suspended in minimal toluene and crashed out with acetone and centrifuged again, this was repeated twice. The solids were left to dry overnight in air. Yield 1.10 g (92.8%)

Example 4

Catalysis of Methanol Production

Experimental Conditions:
3:1 $H_2:CO_2$ at 55 bar pressure and 250 C was used. The catalysts are suspended in 100 mL of squalane and loaded into a batch reactor. The reaction is monitored by taking aliquots from the reactor head space via a heated transfer line and analysing the gas composition using GC. The catalysts for the reactions are zinc oxide nanoparticles and mixtures of zinc oxide and copper nanoparticles.

A range of solvents can be used to prepare a colloidal solution of surface-functionalised nanoparticles for use to catalyse the production of methanol. A solvent may be selected for optimal compatibility with the surface-functionalised nanoparticle, depending on the solubility/chemical nature of X and the polarity of the underlying particle. In this example, squalane was used.

TABLE 3

| Catalyst | MeOH (umol/ghr) |
| --- | --- |
| ZnO with stearate capping ligands (5:1 from diethyl zinc:zincbis(stereate)) | 1.0 |
| ZnO with dioctyl phosphinate capping ligands (5:1, diethyl zinc: dioctyl phosphinic acid) | 1.0 |
| Cu(0) nanoparticles and ZnO nanoparticles with stereate capping ligands (1:1 by mass of the metal) | 50 |

Entry 1: 130 mg of ZnO nanoparticles with stearate capping ligands were dissolved in squalane so as to make a solution of 300 mg total mass. This was added to 100 mL of squalane in the reactor and screened for methanol activity.

Entry 2: 215 mg of nanoparticles were dissolved in squalane so as to make a solution of total mass 500 mg. This was added to 100 mL of squalane in the reactor and screened for methanol activity.

Entry 3: 9.5 mg of copper nanoparticles were dissolved in squalane so as to make a 95 mg solution by mass. This was mixed with 100 mg of the zinc oxide with stearate capping ligand solution (entry 1). The solutions were added to 100 mL of squalane and screened for methanol activity.

Example 5

Carbon Dioxide Hydrogenation

Investigations were carried out on catalyst systems formed from surface-functionalised ZnO nanoparticles and ligand-capped Cu nanoparticles.
Preparation of ZnO Nanoparticles with Stearate Ligands:
Under an inert atmosphere, $ZnEt_2$ (247 mg, 2.0 mmol) and zinc stearate (140 mg, 0.22 mmol) were added to dry toluene (8.6 mL) to make a suspension (0.15 M). This was left to stir for 16 h, then heated gently until colourless. A solution of water (72 mg, 4.0 mmol) in acetone (4.7 mL, 0.87 M solution of water) was added to the solution, slowly, over 5 minutes. The solution changed to a yellow colour, then formed a gel and finally a cloudy suspension was evolved. This was stirred for 1 h before being transferred to a centrifuge tube, and further precipitated with acetone. The product was separated by centrifugation (20 min 3900 rpm) and washed twice with toluene (4 mL) and acetone (15 mL). The white powder was air-dried in the centrifuge tubes. Yield 293 mg (96%).
Preparation of ZnO Nanoparticles with Di(Octyl)Phosphinate Ligands:
Di(octyl) phosphinic acid (500 mg, 1.72 mmol) was dried under vacuum for 1 h, dry toluene (57.5 mL) and $ZnEt_2$ (882 µL, 8.61 mmol) was added to make a 0.15 M solution. This was left to stirring for 20 h, before a solution of water (310 mg, 17.22 mmol) in acetone (0.4 M, 43 mL) was added to it, slowly, over 10-15 minutes. The solution turned a pale yellow colour, then formed a translucent gel and finally evolved a cloudy suspension. This was stirred for a further 2 h, before being transferred to a centrifuge tube, and further solid precipitated by the addition of acetone. The product was separated by centrifugation (20 min, 3900 rpm) and washed twice with toluene (4 mL) and acetone (15 mL). The product was air-dried in the centrifuge tubes for 20 h, forming a translucent pellet which was ground with a mortar and pestle to yield a white powder. Yield 1.10 g (93%). These nanoparticles were used in catalysis investigations.

An alternative synthesis involving reacting diethyl zinc with sub-stoichiometric quantities (0.11 eq) of zinc bis(di (octyl)phosphinate) was also investigated. Both syntheses yielded ZnO nanoparticles with average particle diameters of 3-4 nm and narrow polydispersity, as observed by TEM.

TEM images of the zinc oxide nanoparticles showed that the size control was excellent, with average particle diameters ~3-4 nm, narrow polydispersity and well dispersed particles, in an analogous manner seen for stearate capped ZnO particles. X-ray diffraction showed that crystalline, wurtzite zinc oxide had been formed. XRD peaks at low angles were assigned to the octyl chains of the phosphinic capping ligands. The particles were also characterized using UV-vis spectroscopy, where the absorption band below 375 nm, corresponding to ZnO, was clearly observed. The particle sizes were determined using TEM, XRD and UV-Vis spectroscopy, all of which gave values in the range 3-4 nm.

Figure 8:
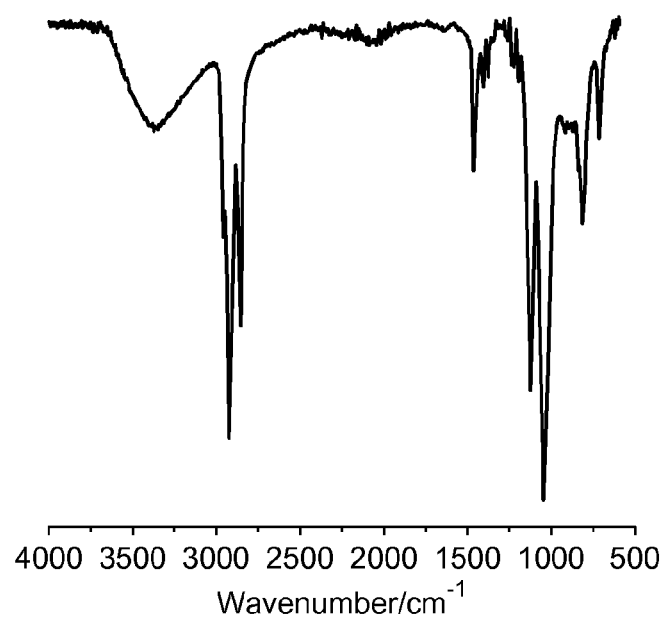
FIG. 8 shows an ATR-FTIR spectrum of zinc oxide nanoparticles prepared using 0.2 eq. of di(octyl)phosphinic acid (vs. $Et_2Zn$).

The presence of the di(octyl)phosphinate group was confirmed by TGA, under an atmosphere of artificial air (20% oxygen, 80% nitrogen), which showed a single weight loss from 280-500° C. Particles prepared using 0.2 eq. of di(octyl)phosphinic acid (vs. Et$_2$Zn) and with particle sizes of 3-4 nm, are calculated to have 37% (w/w) phosphinate composition; the TGA results are in excellent agreement with this calculated proportion, showing 35% (w/w) mass loss. The zinc oxide nanoparticles are soluble in a range of hydrocarbon solvents, such as toluene (16 mgmL$^{-1}$, 298 K), showing higher solubility than the stearate analogues, which required reflux conditions (384 K) to dissolve in toluene. $^{31}$P{$^1$H} NMR spectrum, in CD$_2$Cl$_2$, of a solution of the nanoparticles shows a single resonance at 57 ppm. This resonance is shifted vs. free dioctyl phosphinic acid (60 ppm) and compared to zinc bis(di(octyl)phosphinate) (52 ppm). The NMR data indicate that the phosphinate groups are coordinated to the zinc oxide surface. Further support for phosphinate ligand coordination comes from the infrared spectrum, of the nanoparticles (FIG. 8), which shows two ν(PO) stretches at 1050 and 1130 cm$^{-1}$, the observation of two stretches (vs. one at 970 cm$^{-1}$ for free di(octyl)phosphinic acid) is consistent with di(octyl)phosphinate being coordinated to the zinc oxide surface. The IR spectrum also shows a broad peak at ~3400 cm$^{-1}$ indicating the presence of surface hydroxyl/water groups.

Copper(0) Nanoparticles with Stearate Ligands:

A suspension of copper(II) stearate (2.65 g, 4.20 mmol) in squalane (80 mL) was heated until complete dissolution, then N$_2$H$_4$ (0.269 g, 8.40 mmol, as a 1 M solution in THF) was added slowly over 5 minutes. The mixture was then heated, under nitrogen, at 60° C. for 16 h, after which the dark red solution was placed under vacuum for 3 hours to remove any excess hydrazine. The resulting deep red solution of copper nanoparticles could be stored, under a nitrogen atmosphere, for weeks without any noticeable degradation, as evidenced by UV-Vis and visual inspection (>8 weeks). UV-Vis spectroscopy confirmed the formation of <10 nm sized copper nanoparticles. TGA of the nanoparticles confirmed the presence of the stearate ligand, with ~90% mass loss between 200 and 300° C. corresponding well to the calculated particle composition (Cu=11%). The TEM images of the nanoparticles showed most of the particles were very small (diameters <1 nm), some larger aggregates (d<10 nm) were also observed.

Copper(0) Nanoparticles with Di(Octyl) Phosphinate Ligands:

A suspension of copper(II) bis(di(octyl)phosphinate) (0.17 g, 0.27 mmol) in squalane (80 mL) was heated until complete dissolution, then N$_2$H$_4$ (0.5 mL, 0.58 mmol, as a 1 M solution in THF) was added slowly over 5 minutes. The mixture was then heated, under nitrogen, at 333 K for 4 h, after which the dark red/brown solution was placed under vacuum for 3 hours to remove any excess hydrazine and THF.

Carbon Dioxide Hydrogenation Catalytic Testing

A 300 mL stainless steel Parr reactor was filled with squalane (100 mL) and the appropriate mass of ZnO particles was added, the mixture was then stirred at 298 K, under a flow of N$_2$ (350 mLmin$^{-1}$), for 30 minutes. Whilst under the flow of N$_2$, an aliquot of the Cu(0) solution in squalane (4 mL) was added and the mixture stirred at 298 K for a further 10 minutes. The reactor was then charged with the reaction gas mixture and the vessel heated to the reaction temperature.

Catalytic runs were conducted in a CSTR reactor using gas mixtures H$_2$:CO$_2$ (3:1 combined flow rate 166 mLmin$^-$1), pressurised to 50 bar and heated to 523 K. Squalane has a high boiling point and possesses good gas solubility of the feed gases. In addition, the use of non-polar solvents promotes methanol production. The product flow and unreacted material was continuously monitored by online GC (Varian 450-GC Gas Chromatograph, using a PACKED SS COL ⅛"×2 m Porus Polymer (Haysap C) 80/100. A heated (523 K) transfer line of ⅛" 316 steel was used to connect to the autoclave.

The major hydrocarbon product was methanol, but carbon monoxide was also detected. Mixing solutions of the two nanoparticles together yielded an efficient system for methanol synthesis. Catalytic activity is shown in Table 4.

TABLE 4

Catalytic activities of stearate capped ZnO and Cu nanoparticles for methanol production at different proportions, by weight, of ZnO/Cu.

| Catalyst System[a] | Relative Proportions, by weight, of ZnO:Cu[b] | Peak Activity/μmolg$^{-1}$h$^{-1c}$ |
|---|---|---|
| ZnO:Cu(0) | 50:50 | 4931 |
| ZnO:Cu(0) | 65:35 | 6275 |
| ZnO:Cu(0) | 75:25 | 2549 |

[a]Reaction conditions: 523K, 50 bar (3:1, H2:CO2), in squalane at a fixed total volume of 104 mL, a flow of 166 mLmin-1 over 16 h.
[b]The relative masses (weight ratio) of ZnO present in each solution of stearate capped ZnO nanoparticles were determined according to m(ZnO) = m(nanoparticles) × 0.38, where 0.38 is determined from the 62% mass loss observed in TGA due to the pyrolysis of the stearate group. The mass of Cu present was determined according to m(Cu) = m(Cu(0) solution) × 0.1, where 0.1 is determined from the 90% mass loss (adjusted for Cu content in CuO) observed in the TGA due to the pyrolysis of the stearate group. Weight ratio may be confirmed by elemental analysis.

The catalysts were all active from the start of the reaction, but showed activation periods of approximately 2 hours (at which point the peak activity is reported). During the period of 2-16 hours there is a small activity decrease, corresponding to 1-4% of the peak value. For the stearate-capped ZnO and Cu catalyst system, the ratio of ZnO:Cu influences the catalytic activity, with the highest values resulting from a loading of 65:35 ZnO:Cu (w/w).

Promising catalytic activities were exhibited by the ZnO and Cu stearate capped nanoparticles. Some ripening of the ZnO and Cu nanoparticles was observed, leading to deposition of a red precipitate. This ripening presumably occurs due to some reductive instability of the stearate ligand.

Catalyst systems containing dialkyl phosphinates were also prepared and the observed catalytic activity is shown in Table 5.

TABLE 5

Catalytic activities of di(octyl phosphinate) capped ZnO and stearate capped Cu nanoparticles for methanol production at different proportions, by weight, of ZnO/Cu.

| Entry # | Catalyst System[a] | Relative Proportions, by weight, of ZnO:Cu[b] | Peak Activity/μmolg$^{-1}$h$^{-1c}$ |
|---|---|---|---|
| 2 | ZnO(di(octyl)phosphinate): Cu(stearate) | 50:50 | 8584 |
| 3 | ZnO(di(octyl)phosphinate): Cu(stearate) | 65:35 | 20356 |
| 4 | ZnO(di(octyl)phosphinate): Cu(stearate) | 75:25 | 6942 |

TABLE 5-continued

Catalytic activities of di(octyl phosphinate) capped
ZnO and stearate capped Cu nanoparticles
for methanol production at different proportions,
by weight, of ZnO/Cu.

| Entry # | Catalyst System[a] | Relative Proportions, by weight, of ZnO:Cu[b] | Peak Activity/ $\mu molg^{-1}h^{-1}$[c] |
|---|---|---|---|
| 5 | ZnO(di(octyl)phosphinate):Cu(di(octyl)phosphinate) | 65:35 | 1742 |

[a],[c],[d]as for Table 1.

[b]The relative masses of ZnO present in each solution of stearate capped ZnO nanoparticles was determined according to m(ZnO) = m(nanoparticles) × 0.65, where 0.65 is determined from the 35% mass loss observed in the TGA due to the pyrolysis of the phosphinate group. The mass of Cu present was determined as per Table 1. Weight ratio may be confirmed by elemental analysis.

The catalytic activity of mixtures of these di(octyl)phosphinate capped zinc oxide and stearate capped copper nanoparticles were higher than the stearate capped analogues. The post-reaction mixture using di(octyl)phosphinate capped ZnO remained a clear red solution.

Sample Preparation Methods for Analytical Techniques

UV-Vis Spectra of Cu Nanoparticles

A sample suitable for UV-Vis analysis was prepared from a centrifuged sample of the Cu nanoparticles, synthesised as per the earlier description. The squalane suspension of nanoparticles was centrifuged, at 3900 rpm for 20 minutes, and the excess squalane decanted. The process was repeated using dry, de-gassed hexane (twice) and the sample dried under high vacuum. The red powder was then suspended in dry, degassed toluene (approximately 4 mg in 3 mL toluene) and the spectra collected using an air-tight cuvette.

Additional catalyst systems were synthesised in accordance with the procedures described above, utilised in the described hydrogenation and observed to have good catalytic activity. Observed activities are shown in Table 6. The ZnO nanoparticles used had varying DOPA loadings ([X]/[M] ratio) and the catalysts had a 65:35 ZnO:Cu mass ratio.

TABLE 6

Catalytic activities for ZnO:Cu catalyst systems

| Catalyst | [X]/[M] | Activity/$\mu molg_{cat}^{-1}hr^{-1}$ |
|---|---|---|
| Zinc oxide with di(octyl)phosphinate ligands: copper with stearate capping ligands | 0.33 | 17030 |
| Zinc oxide with di(octyl)phosphinate ligands: copper with stearate capping ligands | 0.20 | 20356 |
| Zinc oxide with di(octyl)phosphinate ligands: copper with stearate capping ligands | 0.13 | 10984 |
| Zinc oxide with di(octyl)phosphinate ligands: copper with stearate capping ligands | 0.1 | 8295 |
| Zinc oxide with di(octyl)phosphinate ligands: copper with stearate capping ligands | 0.05 | 9659 |

Example 6

Assessment of reductive stability of ligands

A series of control experiments using only the ZnO nanoparticles, coordinated by either stereate or phosphinate groups, were conducted to investigate the stabilities of the nanoparticles (capping ligands) to the reaction conditions. Thus, squalane solutions of the zinc oxide nanoparticles were subjected to the reaction conditions (523 K, 50 bar (3:1, $H_2$:$CO_2$), a flow of 166 mLmin$^{-1}$ over 16 h). TEM images before and after the reaction showed changes to the stearate capped particles with significant ripening and aggregation of the particles being observed. In contrast, the phosphinate capped particles remain as discrete small nanoparticles even after heating, under the reaction conditions, for extended periods. Furthermore, a study of the nanoparticles using ATR-IR spectroscopy, again under the reaction conditions, revealed changes to the coordination modes of the stearate moieties which were not observed in the case of phosphinate capped particles. These control experiments, therefore, illustrate the improved reductive stability of the phosphinate capped ZnO nanoparticles.

The relative reductive stability of ligands was assessed by putting liganded ZnO nanoparticles in the reactor as described above and in example 6 under $H_2$ at the reaction temperature and seeing how fast the system ripens/agglomerates/precipitates, with faster ripening/agglomeration/precipitation indicating lower reductive stability. This test could be replicated in any corresponding hydrogenation reactor to determine relative reductive stabilities.

Embodiments of the invention have been described by way of example only. It will be appreciated that variations of the described embodiments may be made which are still within the scope of the invention.

The invention claimed is:

1. A process for the preparation of surface-functionalised metal oxide or metal chalcogenide nanoparticles, the process consisting of:
    (a) providing a precursor mixture in a hydrocarbon solvent comprising a first organometallic precursor comprising a metal centre M and one or more hydrolysable organic ligands $R^a$, and a source of a non-hydrolysable ligand X, wherein the molar loading, [X]/[M], within the precursor mixture is from 0.001 to 0.4;
    wherein:
    each $R^a$ is independently selected from the group consisting of optionally substituted aliphatic groups, aryl, aralkyl, amido, alkoxide, aryloxide, and thiolate;
    each X is independently a ligand comprising a moiety selected from the group consisting of a carboxylate, a thio-carboxylate, a dithiocarboxylate, a sulphate, a sulfonate, a sulphinate, a phosphonate, a phosphinate, a halide, an amide, a carbonate, a dithiocarbonate, an amine, and a nitrate; and
    M is selected from the group consisting of Zn, Al, Ti, Sn, Mg, Ca, Ga, Y, Sc, Zr, Ge, In, and lanthanides, or a mixture thereof;
    and
    (b) exposing the precursor mixture to $H_2E$, wherein E is O, S, Se or Te, to produce surface-functionalised metal oxide or metal chalcogenide nanoparticles in solution.
2. The process of claim 1, wherein X is a carboxylate of formula OOCR$^b$ or a phosphinate of formula (O(O)PR$^b{}_2$), wherein each R$^b$ is, independently, alkyl, aryl or aralkyl.

3. The process of claim 1, wherein the source of ligand X is XH or an organometallic compound with metal centre M and one or more ligands X.

4. The process of claim 1, wherein the molar loading [X]/[M] in the precursor mixture is from 0.001 to 0.35.

5. The process of claim 1, wherein the precursor mixture further comprises a doping amount of a second metal, selected from the group consisting of Ga, Al, Li, Na, K, Cr, or a lanthanide, present at <10%, calculated on the basis of an atom% (in metal) in relation to total M in the precursor mixture.

* * * * *